(12) United States Patent
Farmer et al.

(10) Patent No.: US 8,859,822 B2
(45) Date of Patent: Oct. 14, 2014

(54) SYNTHESIS OF SUBSTITUTED SALICYLALDEHYDE DERIVATIVES

(75) Inventors: Jay J. Farmer, Ithaca, NY (US); Gabriel E. Job, Lansing, NY (US)

(73) Assignee: Novomer, Inc., Ithaca, NY (US)

( * ) Notice: Subject to any disclaimer, the term of this patent is extended or adjusted under 35 U.S.C. 154(b) by 19 days.

(21) Appl. No.: 13/825,548

(22) PCT Filed: Sep. 22, 2011

(86) PCT No.: PCT/US2011/052748
§ 371 (c)(1),
(2), (4) Date: Mar. 21, 2013

(87) PCT Pub. No.: WO2012/040454
PCT Pub. Date: Mar. 29, 2012

(65) Prior Publication Data
US 2013/0197223 A1 Aug. 1, 2013

Related U.S. Application Data

(60) Provisional application No. 61/385,551, filed on Sep. 22, 2010.

(51) Int. Cl.
*C07C 45/00* (2006.01)
*C07D 487/04* (2006.01)
*C07D 221/00* (2006.01)
*C07D 519/00* (2006.01)
*C07D 493/08* (2006.01)

(52) U.S. Cl.
CPC ............ *C07D 487/04* (2013.01); *C07D 221/00* (2013.01); *C07D 519/00* (2013.01); *C07D 493/08* (2013.01)

USPC .......................................................... 568/426

(58) Field of Classification Search
CPC ........................................................ C07C 45/00
USPC .......................................................... 568/426
See application file for complete search history.

(56) References Cited

FOREIGN PATENT DOCUMENTS

WO    WO 2010/022388 A2    2/2010

OTHER PUBLICATIONS

Ragot et al., A Novel Route to Preussomerins via 2-Arylacetal Anions, Organic Letters, 2(11):1613-1616 (2000).
International Search Report for PCT/US2011/052748, 2 pages (Mar. 15, 2012).
Voleva et al., Synthesis and Structure of Anhydrodimers of Salicylaldehyde, Russian Chemical Bulletin, 44(8):1489-1491 (1995).
International Preliminary Report on Patentability for PCT/US2011/25748, 5 pages (Oct. 22, 2012).

*Primary Examiner* — Nizal Chandrakumar
(74) *Attorney, Agent, or Firm* — Choate, Hall & Stewart LLP; Charles E. Lyon; John P. Rearick

(57) ABSTRACT

Among other things, the present invention encompasses methods of synthesizing salicylaldehyde derivatives comprising the steps of: a) providing salicylaldehyde or a derivative thereof, b) forming an anhydro dimer of the provided salicylaldehyde compound, c) performing one or more chemical transformations on the anhydro dimer and d) hydrolyzing the anhydro dimer to provide a salicylaldehyde derivative different from that provided in step (a).

19 Claims, No Drawings

SYNTHESIS OF SUBSTITUTED SALICYLALDEHYDE DERIVATIVES

CROSS REFERENCE TO RELATED APPLICATIONS

The present application is a national phase application under 35 U.S.C. 371 of International Application No. PCT/US2011/052748, filed Sep. 22, 2011, which claims priority to U.S. provisional application Ser. No. 61/385,551, filed Sep. 22, 2010, the entire contents of each of which are hereby incorporated herein by reference.

FIELD OF THE INVENTION

The invention pertains to the field of chemical synthesis. More particularly, the invention pertains to methods for the synthesis of substituted salicylaldehyde derivatives using an anhydro dimer intermediate.

BACKGROUND

Salicylaldehyde 1 and its derivatives (e.g., wherein R is other than hydrogen) are widely used chemicals finding applications in many fields including the synthesis of pharmaceuticals and other biologically active molecules and in the formation of ligands for organometallic compounds used in catalysis and other processes.

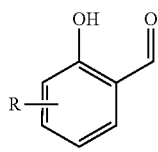

1

The synthesis of salicylaldehyde derivatives is frequently challenging and many cases are documented in which reactions that work well on other phenyl derivatives provide poorer yields when applied to salicylaldehyde systems. Without being bound by any theory or thereby limiting the scope of the present invention, it is believed that the poor yields are often due to interactions of the phenol and aldehyde either via intermolecular reactions to form dimeric materials and oligomers or via undesired interactions of these functional groups with reagents or intermediates employed in attempts to affect chemistry elsewhere on the salicylaldehyde derivatives. A common approach to this problem is to synthesize a substituted phenol bearing the functionality required in the final salicylaldehyde derivative and then perform a formylation reaction to introduce the aldehyde group ortho to the phenolic oxygen to form the required salicylaldehyde. Unfortunately, such formylation reactions often suffer from moderate yields and/or the formation of undesired side-products. The present invention provides a solution to this and other related problems.

Bicyclic anhydro dimers of salicylaldehyde were described and their structures elucidated as early as the 1920s [(i) Lindemann, H.; Forth, H. *Liebigs Ann. Chem.* 1924, 219-232. (ii) Adams, R.; Fogler, M. F.; Kreger, C. W. *J. Am. Chem. Soc.* 1922, 44, 1126-1133. (iii) Newman, M. S.; Pinkus, A. G. *J. Org. Chem.* 1954, 19, 996-1002. (iv) Jones, P. R.; Gelinas, R. M. *J. Org. Chem.* 1981, 46, 194-196. (v) Ragot, J. P.; Prime, M. E.; Archibald, S. J.; Taylor, R. J. K. *Org. Lett.* 2000, 2, 1613-1616. (vi) Vol'eva, V. B.; Belostotskaya, I. S.; Shishkin, O. V.; Struchkov, Y. T.; Ershov, V. V. *Russ. Chem. Bull.* 1995, 44, 1489-1491.]. Additional interest in anhydro dimers was prompted by the identification of the ring system in a family of natural products known collectively as preussomerins, however they have not heretofore been utilized as masked salicylaldehyde intermediates in the syntheses of substituted salicylaldehyde derivatives.

SUMMARY OF THE INVENTION

The present invention encompasses the recognition that anhydro dimers of salicylaldehyde and its derivatives can act as convenient synthetic intermediates that mask the reactivity of the ortho-formyl phenol moiety. In certain embodiments, the invention includes methods of intentionally forming these dimers, performing chemistry on the aryl rings or substituents of the dimerized salicylaldehyde derivatives and then hydrolyzing the dimers to liberate two molecules of the transformed salicylaldehyde derivate.

The present invention provides, among other things, methods of synthesizing salicylaldehyde derivatives comprising the steps of: a) providing salicylaldehyde or a derivative thereof, b) forming an anhydro dimer of the provided salicylaldehyde compound, c) performing one or more chemical transformations on the anhydro dimer and d) hydrolyzing the anhydro dimer to provide a salicylaldehyde derivative different from that provided in step (a). The present invention also encompasses methods of making such salicylaldehyde anhydro dimers.

The present invention provides compositions of matter comprising novel salicylaldehyde dimers. In certain embodiments, such salicylaldehyde dimers have particular utility in the synthesis of catalysts and, in particular, of salen-type catalysts. In some embodiments, such salicylaldehyde dimers have particular utility in the synthesis of biologically active molecules.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of enantiomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of enantiomers.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine, (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms. In some embodiments, aliphatic groups contain 1-4 carbon atoms. In some embodiments, aliphatic groups contain 1-3 carbon atoms. In some embodiments, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic or bicyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, the term "3- to 8-membered carbocycle" refers to a 3- to 8-membered saturated or partially unsaturated monocyclic carbocyclic ring. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring. In certain embodiments, the term "$C_{3-20}$ carbocycle" refers to a 3- to 8-membered saturated or partially unsaturated monocyclic carbocyclic ring, or a 7- to 20-membered saturated or partially unsaturated polycyclic carbocyclic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms. In some embodiments, alkyl groups contain 1-4 carbon atoms. In certain embodiments, alkyl groups contain 1-3 carbon atoms. In some embodiments, alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms. In some embodiments, alkenyl groups contain 2-4 carbon atoms. In some embodiments, alkenyl groups contain 2-3 carbon atoms. In some embodiments, alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms. In some embodiments, alkynyl groups contain 2-4 carbon atoms. In some embodiments, alkynyl groups contain 2-3 carbon atoms. In some embodiments, alkynyl groups contain 2 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the term "8- to 14-membered aryl" refers to an 8- to 14-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 10-membered heteroaryl" refers to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur. In some embodiments, the term "3- to 8-membered heterocycle" refers to a 3- to 8-membered saturated or partially unsaturated monocyclic heterocyclic ring having 1 to 2 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

One of ordinary skill in the art will appreciate that the synthetic methods, as described herein, may utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In some embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are described by Greene and Wuts (infra).

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3- to 12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-4}C(O)N(R^\circ)_2$; —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, —NNHC(O)OR*, —NNHS(O)$_2$R*, =NR*, —NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

In some chemical structures herein, substituents are shown attached to a bond which crosses another bond of a depicted molecule. This means that one or more of the substituents may be attached to the molecule at any available position (usually in place of a hydrogen atom of the parent structure). In cases where an atom of a molecule so substituted has two substitutable positions, two groups may be present on the same atom. When more than one substituent is present, each is defined independently of the others, and each may have a different structure. In cases where the substituent shown crossing a bond of the molecule is —R, this has the same meaning as if the ring were said to be "optionally substituted" as described in the preceding paragraph.

The term "salicylaldehyde" as used herein means any substituted or unsubstituted 2-hydroxybenzaldehyde.

The term "anhydro dimer" as used herein, refers to a molecule formed from the reaction of two molecules of an ortho formyl phenol via the loss of water. While this dimer is shown in the specification to have a specific defined structure, the methods disclosed herein are not limited to this precise structure and therefore encompass other dimeric or pseudodimeric compounds that might be formed.

The term "chemical transformation" as used herein, refers to any chemical reaction that may be performed on an anhydro dimer. In some embodiments, such chemical transformations do not cause a substantial degree of undesirable reaction on the bicyclic acetal moiety of the anhydro dimer and that any functional groups introduced are substantially compatible with the chemistry employed in hydrolysis of the dimers to recover the salicylaldehyde products. In some embodiments, chemical transformations performed on anhydro dimers include carbon-carbon bond forming reactions such as alkylations, arylations and acylations; carbon-heteroatom bond forming reactions including, but not limited to halogenation, nitration, oxidation, silylation, metallation, and the like, as well as transformations of functional groups present on the aryl rings including, but not limited to: oxidations, reductions, additions, protections, deprotections, cycloadditions, aminations, decarboxylations, Click reactions, transition metal-catalyzed couplings, metatheses, alkylations, esterifications, hydrogenations, coupling reactions and the like.

TBD, as used herein refers to 1,5,7-Triazabicyclo[4.4.0]dec-5-ene.

DETAILED DESCRIPTION OF CERTAIN EMBODIMENTS

In one aspect, the present invention encompasses methods of synthesizing salicylaldehyde derivatives comprising the steps of: a) providing salicylaldehyde or a derivative thereof, b) forming an anhydro dimer of the provided salicylaldehyde compound, c) performing one or more chemical transformations on the anhydro dimer and d) hydrolyzing the anhydro dimer to provide a salicylaldehyde derivative different from that provided in step (a).

In some embodiments, a provided method comprises the steps of a) providing salicylaldehyde or a derivative thereof, and b) forming an anhydro dimer of a provided salicylaldehyde compound. In certain embodiments, a provided method further comprises the step of performing one or more chemical transformations on an anhydro dimer. In some embodiments, a provided method further comprises the step of hydrolyzing an anhydro dimer to provide a salicylaldehyde derivative different from that provided in step (a).

In some embodiments, a provided method comprises the steps of a) dehydrating a salicylaldehyde to form an anhydro dimer, b) alkylating at least one aromatic ring of the anhydro dimer in one or more positions; and c) hydrolyzing the alkylated anhydro dimer to recover an alkylated salicylaldehyde derivative.

The formation of an anhydro dimer may be performed using any suitable conditions such as those known in the art. Typical conditions employ acid catalysis in the presence of a dehydrating agent. One such method employs an acid anhydride in the presence of sulfuric or alkyl sulfonic acid catalyst. It will be apparent to the skilled artisan that many other methods can be employed including those based on other dehydrating reagents such as thionyl chloride, phosphorous oxides, dialkyldicarbonates and the like, as well as dehydrating reaction conditions that remove water via azeotroping (Dean Stark or the like) or that rely on adsorbants to physically sequester water (such as molecular sieves, anhydrous salts or the like).

Similarly, hydrolysis of an anhydro dimer to recover the substituted salicylaldehyde may be performed using literature procedures. These normally employ acidic treatment in protic solvents such aqueous mineral acids, but it will be apparent to the skilled artisan that other hydrolysis conditions can be employed. Many examples are available from the literature describing the hydrolysis of acetals and ketals and any of these conditions may be employed in embodiments of the present invention.

Chemical transformations performed at the anhydro-dimer stage can be quite varied, the only limitations being the practical ones requiring that the reagents and conditions employed do not cause a substantial degree of undesirable reaction on the bicyclic acetal moiety of the anhydro dimer and that any functional groups introduced are substantially compatible with the chemistry employed in hydrolysis of the dimers to recover the salicylaldehyde products. In some embodiments, several such reactions are performed on the anhydro dimers prior to recovery of the final substituted salicylaldehyde derivatives by hydrolysis of the dimers.

In certain embodiments, the methods and compounds described herein are useful in the synthesis of known metal complexes and/or ligands thereof. In some embodiments, methods and compounds described herein are useful in the synthesis of compounds described in WO2008136591, WO2010013948, WO2010022388, WO2009137540, WO2008150033, US2010029896, U.S. Pat. Nos. 6,870,004, 7,304,172, JP2010001443A. CN101020747, CN10229276, *J. Am. Chem. Soc.*, 2007, 129, p. 8082-83, *Bull. Korean Chem. Soc.*, 2009, Vol. 30, No. 3 p. 745-748, *Angew. Chem. Int. Ed* 2008, 47, 7306-9, *Angew. Chem. Int. Ed.* 2006, 45, 7274-7277, *J. Am. Chem. Soc.* 2009, p. 11509, and *Macromolecules*, 2010, 43 (3), p. 1396-1402, the entire contents of each of which are hereby incorporated by reference.

I. Carbon-Carbon Bond Forming Reactions

In certain embodiments, a step of performing one or more chemical transformations on an anhydro dimer comprises performing a carbon-carbon bond forming reaction on at least one aromatic ring of the anhydro dimer in one or more positions. In certain embodiments, a carbon-carbon bond forming reaction on at least one aromatic ring of the anhydro dimer comprises alkylating at least one aromatic ring of the anhydro dimer in one or more positions.

In certain embodiments, an alkylation occurs equally on both salicylaldehyde molecules comprising the anhydro dimer. In certain embodiments, this process entails replacing a non-carbon substituent (Q) on the aryl ring with a carbon atom. In certain embodiments, such a method proceeds according Scheme 1:

Scheme 1

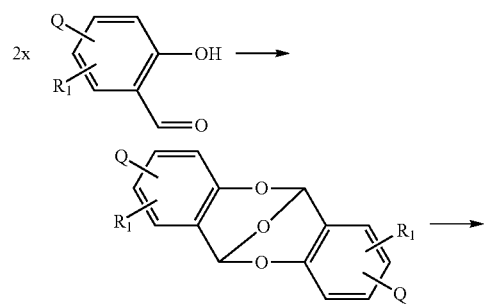

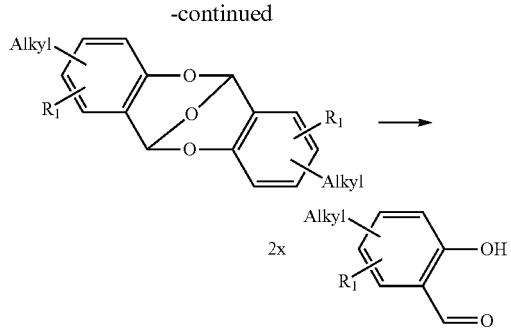

wherein $R_1$ represents one or more non-hydrogen substituents optionally present at one or more positions of the aryl ring(s), where each —$R_1$ group is independently selected and is as defined hereinbelow; -Q represents one or more substitutable groups present on the aryl ring(s) and "-alkyl", represents one or more moieties that is linked to the aryl ring through a carbon atom (including aliphatic, acyl, aryl, etc.) and which is introduced on the aryl ring in place of one or more of the -Q groups.

In certain embodiments, -Q groups in Scheme I are selected from the group consisting of —H, F, Cl, Br, I, —B(OR$^y$)$_2$, —OSO$_2$R$^y$, and combinations of two or more of these.

In certain embodiments, a -Q group in Scheme 1 is —H. In certain embodiments, an —H at the ortho, para or ortho and para positions is replaced with a carbon atom.

In certain embodiments, an alkylation occurs at an unsubstituted aromatic ring position ortho to the hydroxyl group of the starting salicylaldehyde.

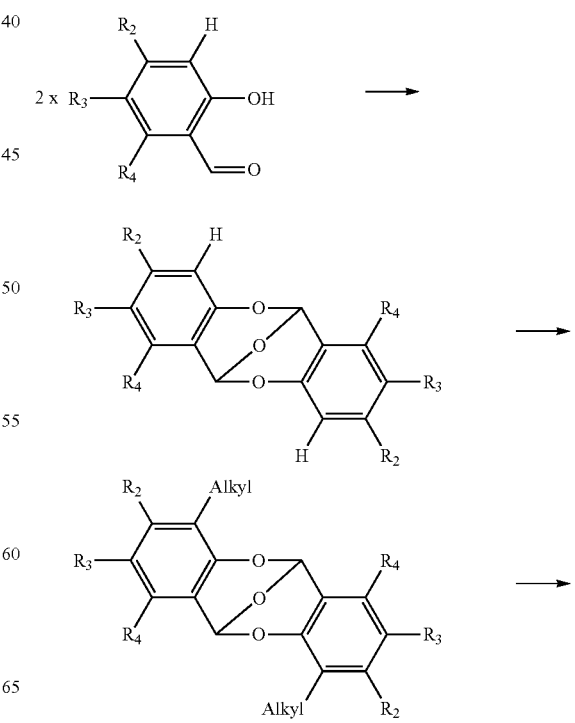

-continued

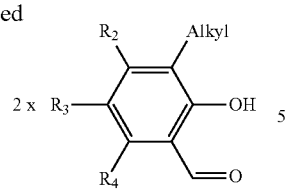

wherein the —$R_x$ groups are as defined hereinbelow and "-alkyl" represents any moiety linked to the aryl ring through a carbon atom (including aliphatic, acyl, aryl, etc.).

In certain embodiments, an alkylation occurs at the aromatic ring position para to the hydroxyl group of the starting salicylaldehyde. In certain embodiments, this process proceeds according to the following scheme:

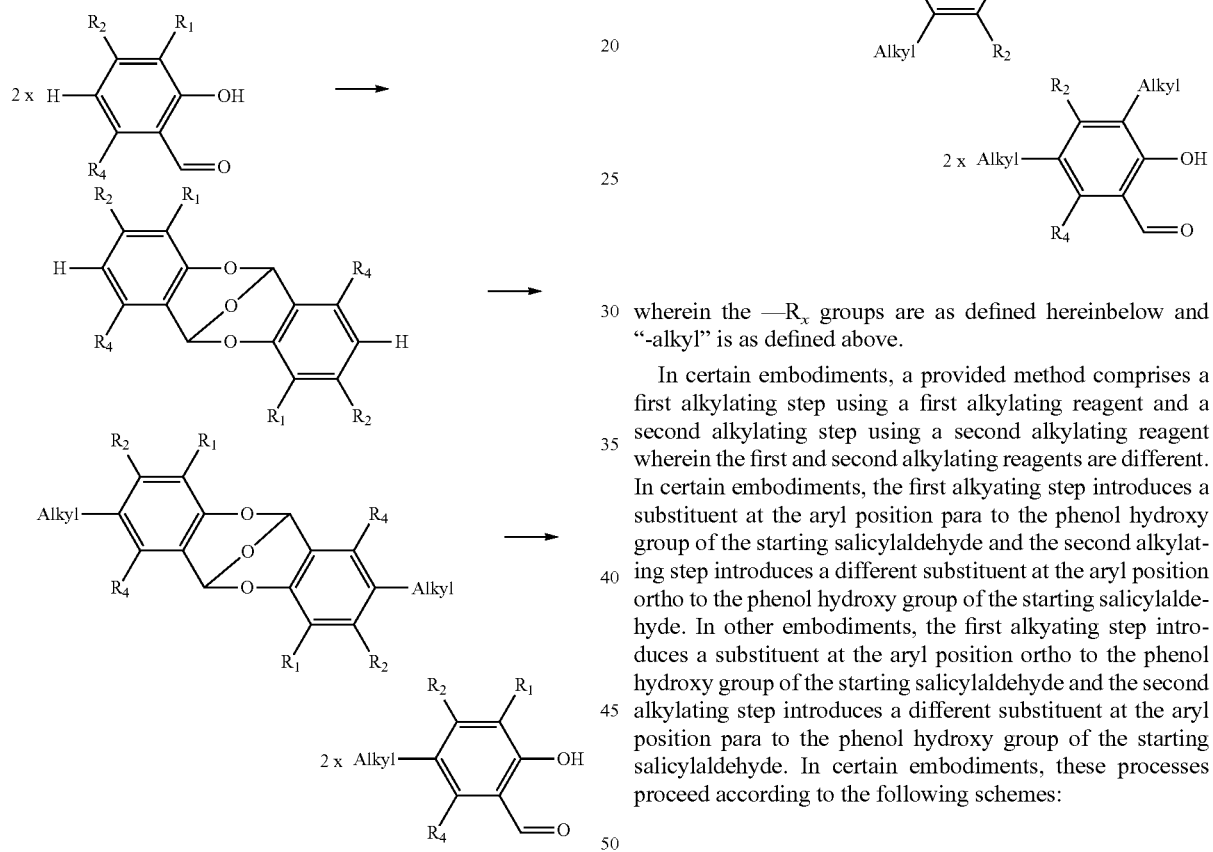

wherein the —$R_x$ groups are as defined hereinbelow and "-alkyl" is as defined above.

In some embodiments, bis alkylation occurs at aromatic ring positions ortho and para to the hydroxyl group of the starting salicylaldehyde. In certain embodiments, this process proceeds according to the following scheme:

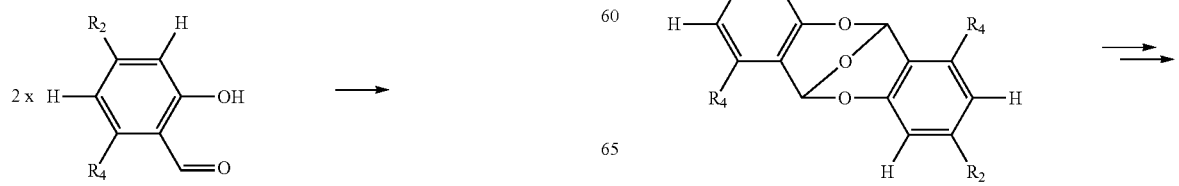

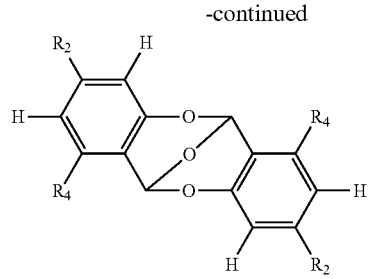

wherein the —$R_x$ groups are as defined hereinbelow and "-alkyl" is as defined above.

In certain embodiments, a provided method comprises a first alkylating step using a first alkylating reagent and a second alkylating step using a second alkylating reagent wherein the first and second alkylating reagents are different. In certain embodiments, the first alkyating step introduces a substituent at the aryl position para to the phenol hydroxy group of the starting salicylaldehyde and the second alkylating step introduces a different substituent at the aryl position ortho to the phenol hydroxy group of the starting salicylaldehyde. In other embodiments, the first alkyating step introduces a substituent at the aryl position ortho to the phenol hydroxy group of the starting salicylaldehyde and the second alkylating step introduces a different substituent at the aryl position para to the phenol hydroxy group of the starting salicylaldehyde. In certain embodiments, these processes proceed according to the following schemes:

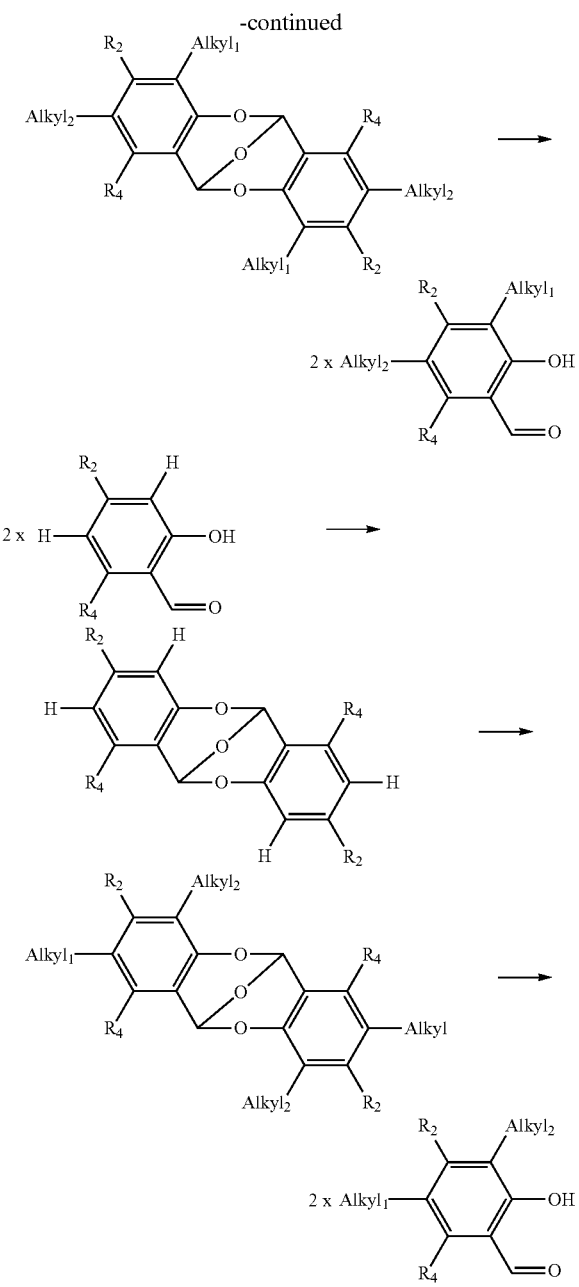

wherein the —R$_X$ groups are as defined hereinbelow and "-alkyl" is as defined above.

In some embodiments, a starting salicylaldehyde is substituted at the aryl position ortho to the phenol and an alkylation step introduces a substituent at the aryl position para to the phenol hydroxyl group.

In some embodiments, a starting salicylaldehyde is substituted at the aryl position para to the phenol and an alkylation step introduces a substituent at the aryl position ortho to the phenol hydroxyl group.

In certain embodiments, an alkylation transforms R$_3$ of an anhydro dimer from —H to an optionally substituted aliphatic group. In certain embodiments, an optionally substituted aliphatic group introduced at R$_3$ is selected from the group consisting of optionally substituted C$_{1-20}$ aliphatic, and optionally substituted aryl.

In certain embodiments, a step of alkylating the aromatic ring comprises reacting the anhydro dimer under Friedel Crafts conditions. In certain embodiments, a step of alkylating the aromatic ring comprises reacting the anhydro dimer under Friedel Crafts alkylating or acylating conditions. Suitable reagents and conditions for Friedel Crafts reactions are well known in the art. Exemplary conditions for such transformations include, but are not limited to, those found in: *ADVANCED ORGANIC CHEMISTRY.* 4$^{th}$ Ed. by Jerry March, pp 534-552 and the references cited therein.

In certain embodiments, the Friedel Crafts alkylating conditions comprise reacting the anhydro dimer with at least one compound selected from the group consisting of: alkenes, alcohols, alkyl halides, and mixtures of two or more of these in the presence of a promoter selected from the group consisting of Lewis acids and proton acids.

In certain embodiments, the step of performing a carbon-carbon bond forming reaction comprises reacting the anhydro dimer with a transition metal catalyst and a suitable reagent to introduce a new carbon-linked substituent. In certain embodiments, such transitional metal catalyzed carbon-carbon bond forming reactions take place between the anhydro dimer and a suitable reagent, wherein the anhydro dimer and reagent bear complementary coupling groups. Suitable coupling reactions are well known to one of ordinary skill in the art and typically involve either the anhydro dimer or reagent bear an electron-withdrawing group (EWG) (e.g., Cl, Br, I, OTf, OTs, OMs etc.), such that the resulting polar carbon-EWG bond is susceptible to oxidative addition by an electron-rich metal (e.g., a low-valent palladium or nickel species), and the complementary coupling group being an electropositive group (e.g., boronic acids, boronic esters, boranes, stannanes, silyl species, zinc species, aluminum species, magnesium species, zirconium species, etc.), such that the carbon which bears the electropositive coupling group is susceptible to transfer to other electropositive species (e.g., a Pd$^{II-IV}$ species or a Ni$^{II-IV}$ species).

In certain embodiments, the step of performing a transition metal-catalyzed carbon-carbon bond forming reaction comprises reacting a position on the anhydro dimer substituted with a halogen, or similar group (i.e. a sulfonate ester or other leaving group) with a transition metal catalyst and a suitable reagent to introduce a new substituent at that position. In certain embodiments, the step of performing a transition metal-catalyzed carbon-carbon bond forming reaction comprises reacting a position on the anhydro dimer substituted with an atom from groups 1-2 or 12-14 (IA-IIA and IIB-IVA) of the periodic table. In certain embodiments, the atom is selected from the group consisting of, boron, tin, silicon, magnesium, or zinc atom with a transition metal catalyst and a suitable reagent to introduce a new carbon-linked substituent at that position. Suitable conditions, catalysts and reagents for performing such transformations are well known in the art. Suitable conditions can be found in *ADVANCED ORGANIC CHEMISTRY.* 4$^{th}$ Ed. by Jerry March and references cited therein.

In some embodiments, the coupling is a Suzuki coupling. Suzuki coupling of boronic acids with different aryl halides is typically conducted using palladium catalysts tetrakis(triphenylphosphine) palladium (0) or another suitable source such as trans-dichlorobis(tri-o-tolylphosphine)palladium (II), Pd(II)Cl$_2$(PPh$_3$)$_2$, Pd(II)Cl$_2$(dppb)$_2$, Pd(II)(OAc)$_2$+PPh$_3$, Pd(II)(OAc)$_2$+tri(o-tolyl)phosphine (palladacycle), or Pd/C under basic conditions. Typically, the reaction base is sodium or potassium or barium hydroxide, sodium or potassium bicarbonate, sodium, potassium, cesium or thallium carbonate, cesium or potassium fluoride sodium or potassium tert-butoxide, potassium phosphate or triethylamine and the solvent includes DMF, ethanol, tetrahydrofuran, dioxane, ethylene glycol dimethyl ether, water, toluene/benzene and mixtures thereof and with phase transfer reagents, such as Bu$_4$NCl or 18-crown-6. Exemplary reactions include those described in *Metal-Catalyzed Cross-Coupling Reactions*, A. de Meijere and F. Diederich, Eds., 2$^{nd}$ Edition, John Wiley & Sons, 2004; and Handbook of *Organopalladium Chemistry for Organic Synthesis*, Negishi, E., de Meijere, A. Editors, Wiley: New York, N.Y., 2002.

II. Carbon-Heteroatom Bond Forming Reactions

In other embodiments, a step of performing one or more chemical transformations on an anhydro dimer comprises performing a carbon-heteroatom bond forming reaction on at least one aromatic ring of an anhydro dimer in one or more positions.

In certain embodiments, a carbon-heteroatom bond forming reaction is selected from the group consisting of halogenation, or introduction of a group linked via an atom selected from the group consisting of: oxygen, nitrogen, sulfur, phosphorous, boron, tin, silicon, lithium, magnesium, or combinations of two or more of these.

In certain embodiments, the anhydro dimer formed in step (a) has a formula:

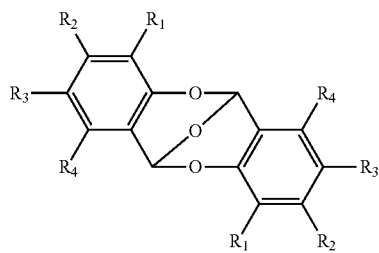

wherein at least one of $R_1$, $R_2$, $R_3$, and $R_4$ is —H, and the remainder are each independently selected from the group consisting of halogen, —NO$_2$, —CN, —Si(R$^y$)$_3$, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$. —N(R$^y$)$_2$, —NR$^y$C(O)R$^y$, —NR$^y$C(O)OR$^y$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated or partially unsaturated carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; 8- to 14-membered aryl; or an 8- to 10-membered bicyclic heteroaryl ring having 1-5 heteroatoms independently selected from nitrogen, oxygen, or sulfur, where each occurrence of R$^y$ is independently —H, or an optionally substituted radical selected from the group consisting of C$_{1-6}$ aliphatic, 3- to 7-membered heterocyclic, phenyl, and 8- to 10-membered aryl, and where two or more adjacent R$^y$ groups can be taken together to form an optionally substituted saturated, partially unsaturated, or aromatic 5- to 12-membered ring containing 0 to 4 heteroatoms.

In certain embodiments, $R_3$ is —H in a provided salicylaldehyde derivative from which an anhydro dimer is formed.

In certain embodiments, $R_1$ in a provided salicylaldehyde derivative selected from the group consisting of optionally substituted C$_{1-20}$ aliphatic, and optionally substituted aryl.

In certain embodiments, $R_1$ in the provided salicylaldehyde derivative from which the anhydro dimer is formed is selected from the group consisting of methyl, ethyl, n-propyl, isopropyl, n-butyl, sec-butyl, t-butyl, isoamyl, tert-amyl, and substituted phenyl.

III. Functional Group Manipulations

It will be appreciated that, in addition to reactions that add or modify substituents on the anhydro dimers, the present invention encompasses chemical manipulations to the anhydro dimer substituent groups themselves. In certain embodiments, the step of performing one or more chemical transformations on the anhydro dimer comprises performing one or more chemical reactions to manipulate functional groups already present on the anhydro dimer. Such reactions can include those commonly performed in organic synthesis such as reductions, oxidations, additions, protections, deprotections, cycloadditions, aminations, decarboxylations, halogenations, transition metal-catalyzed carbon-carbon bond couplings, Click reactions, ring-closing or cross metathesis reactions, and the like. The functional groups thus manipulated may be those attached to the aryl ring of the salicaldehyde or may be present on substituents attached to the aryl rings.

The following schemes represent non-limiting examples of chemical syntheses embodying certain methods of the present invention. Such chemical transformations and useful reagents for carrying out such reactions will be known to the skilled artisan, and are also available in the literature (e.g. March, vide supra).

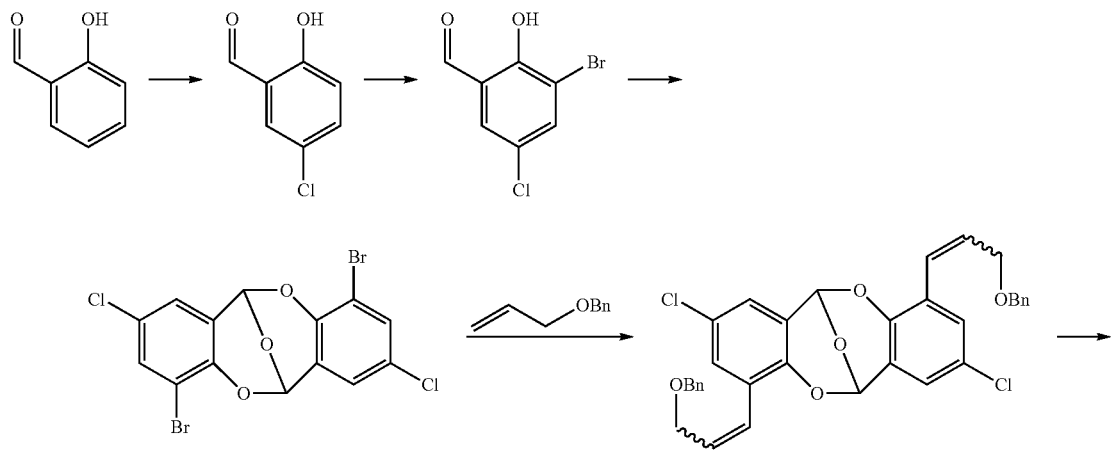

-continued
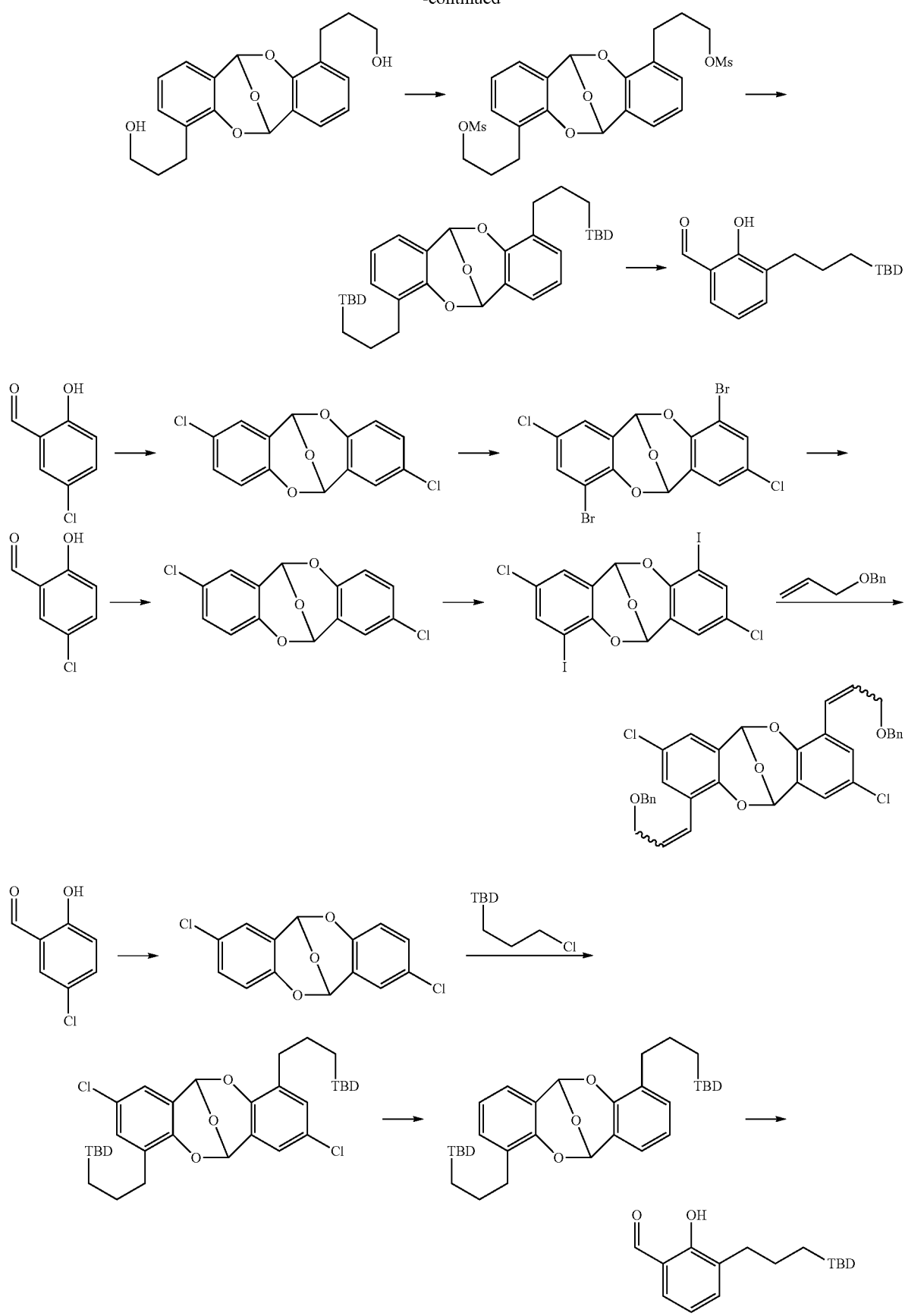

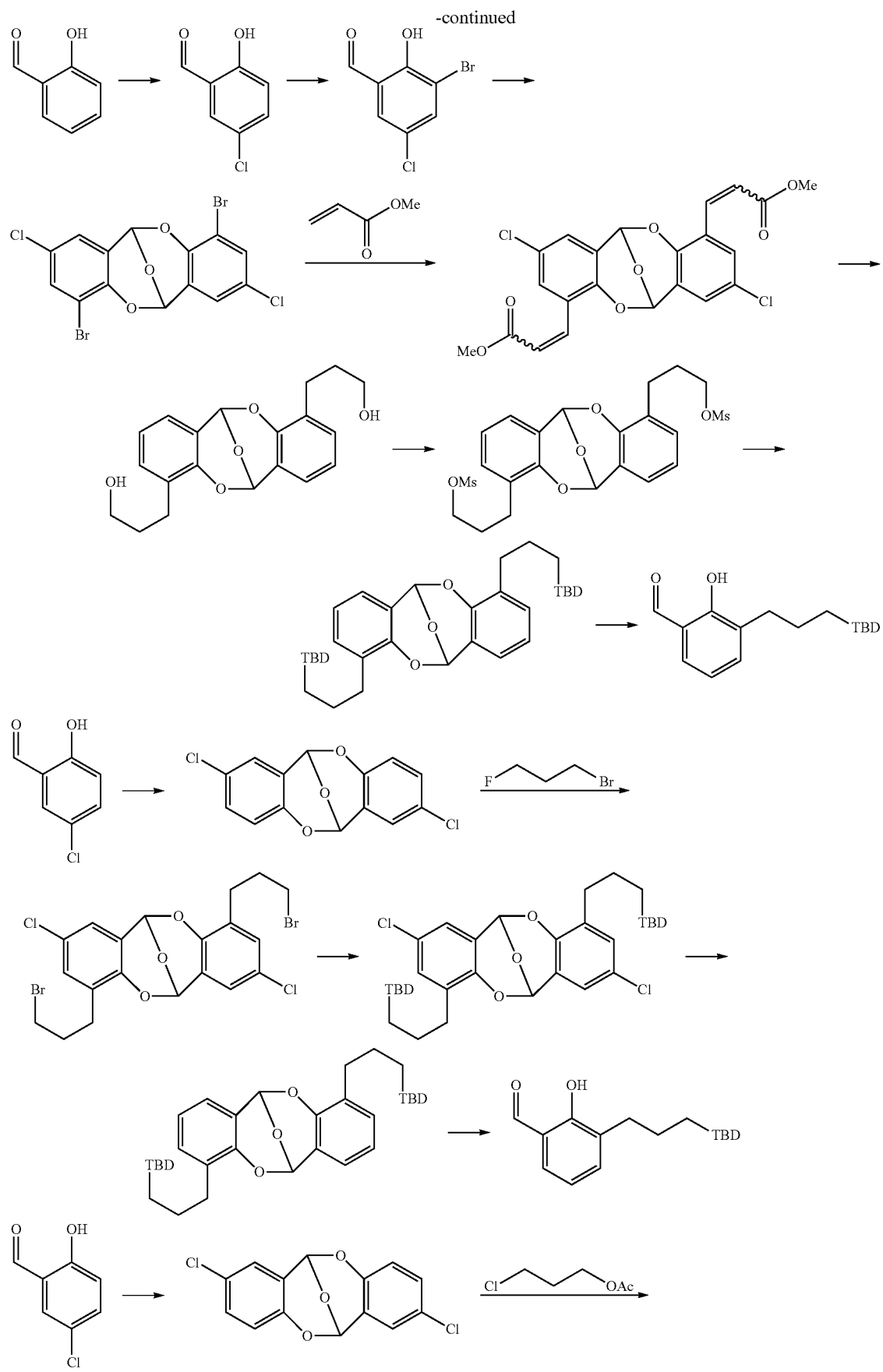

23
-continued
24
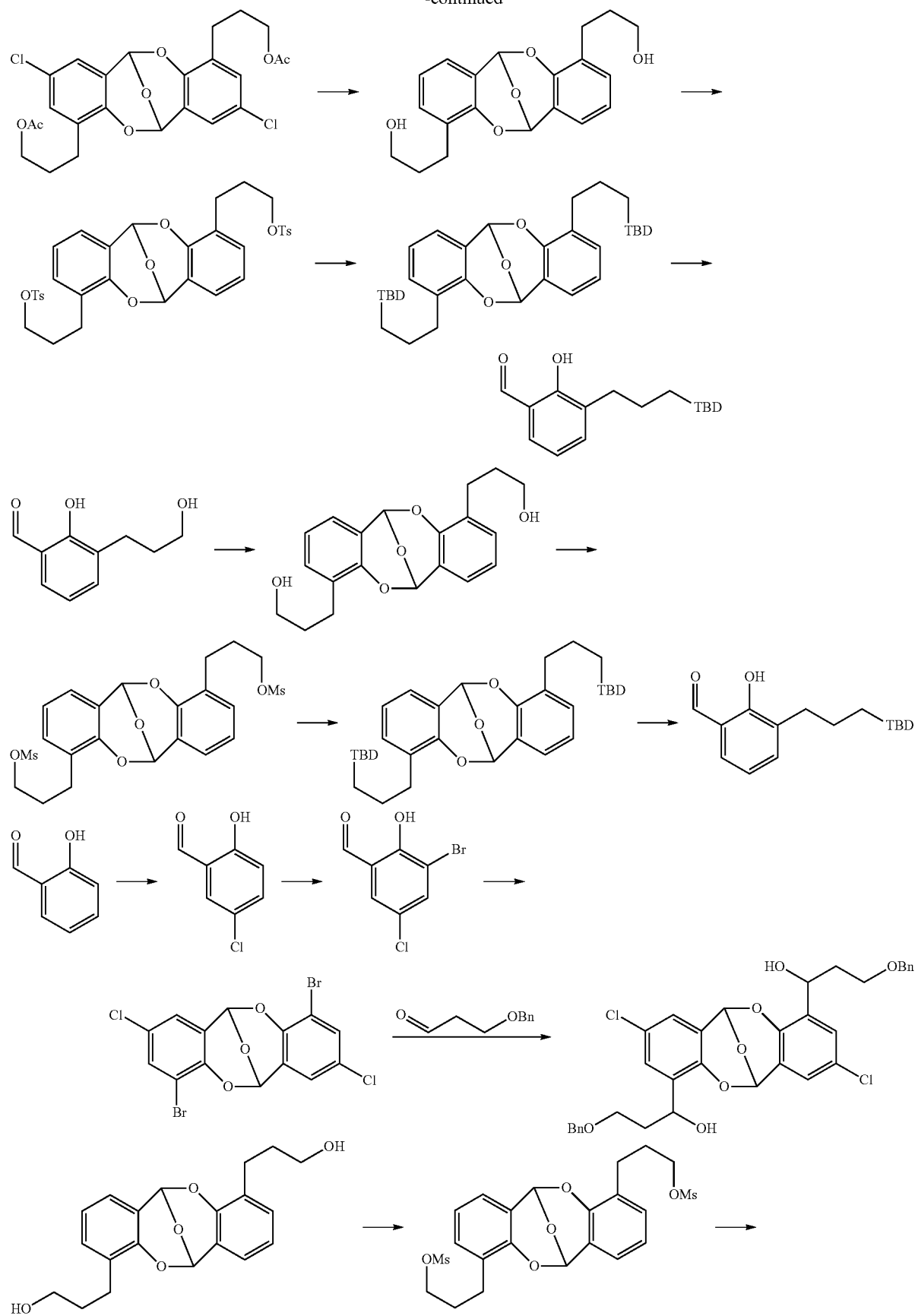

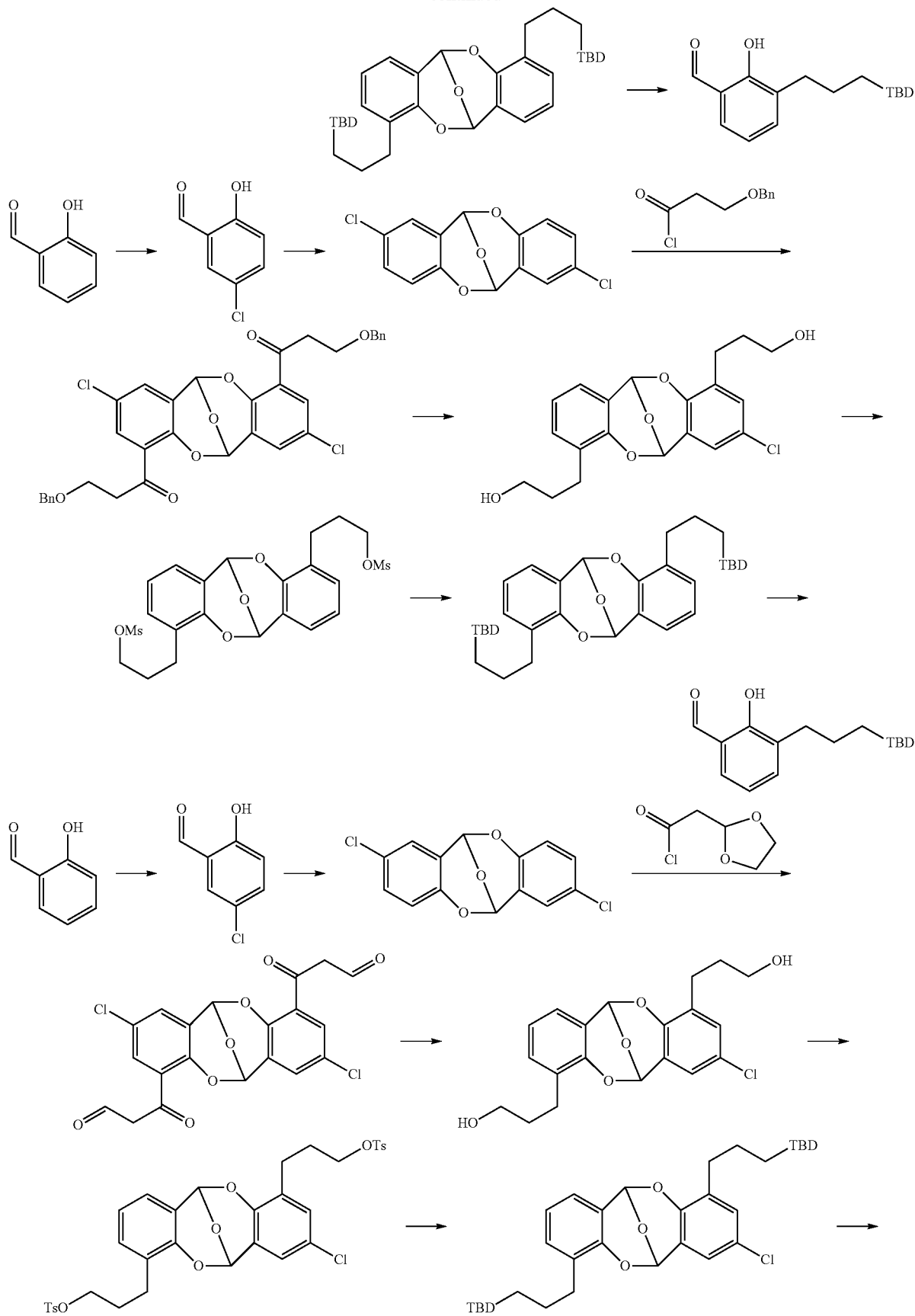

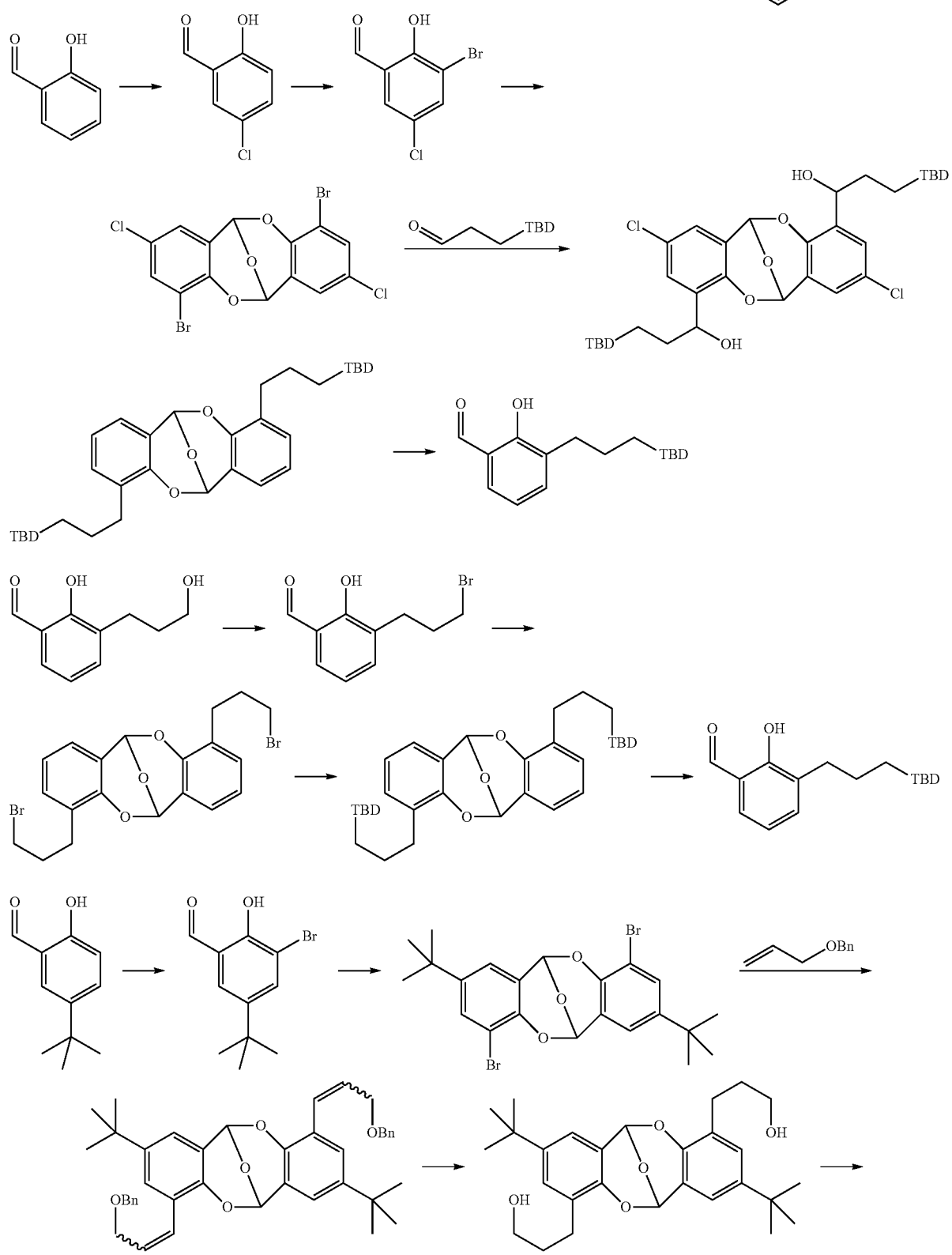

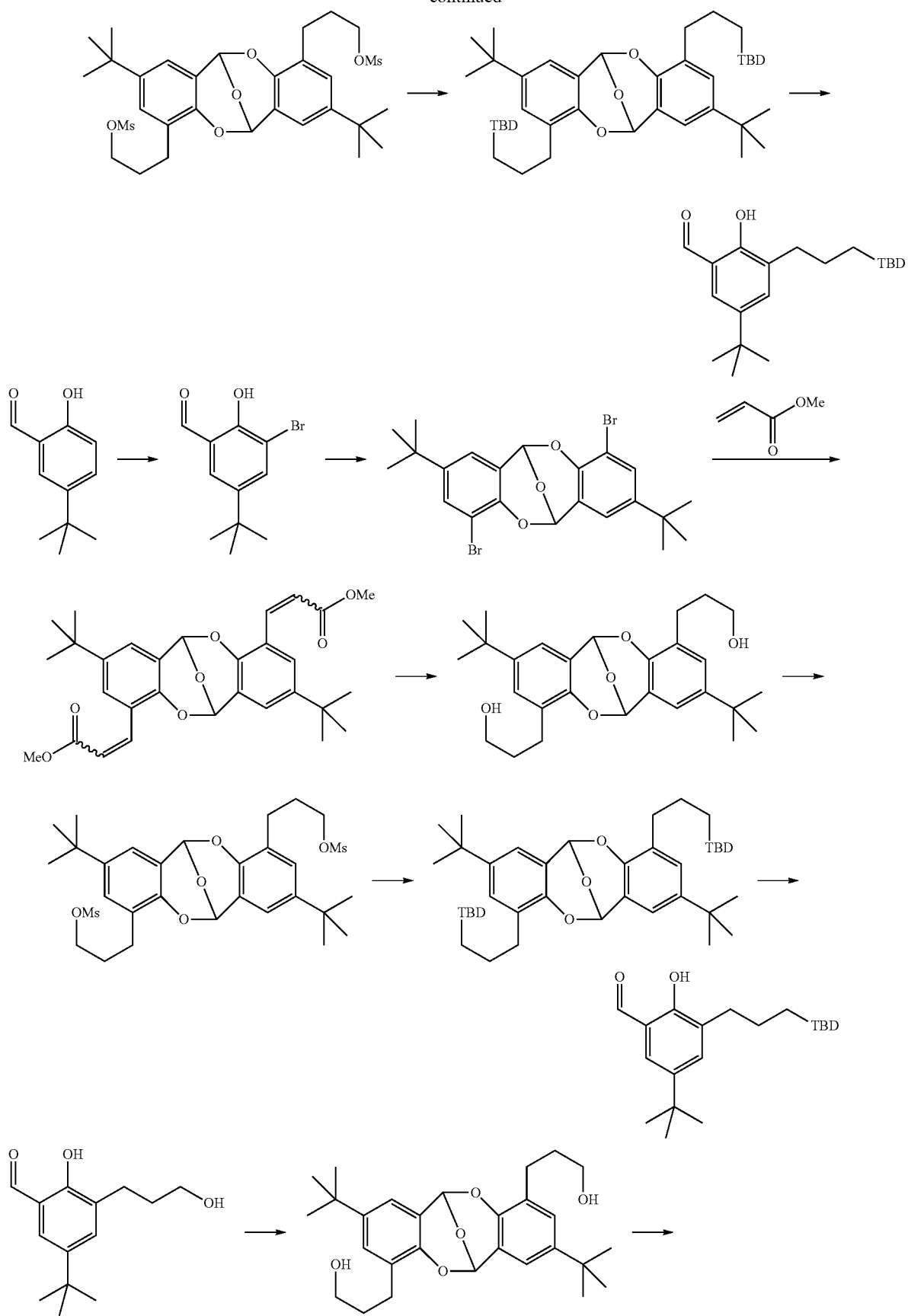

31        -continued        32
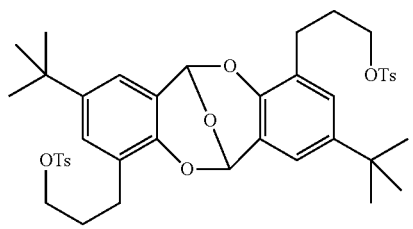 → 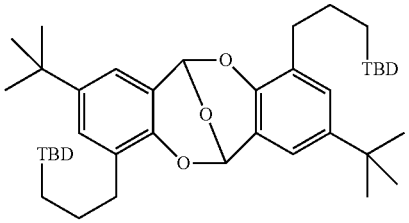 →
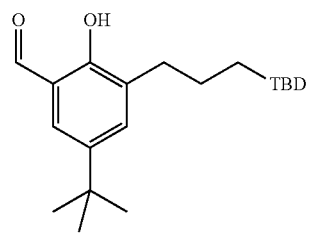
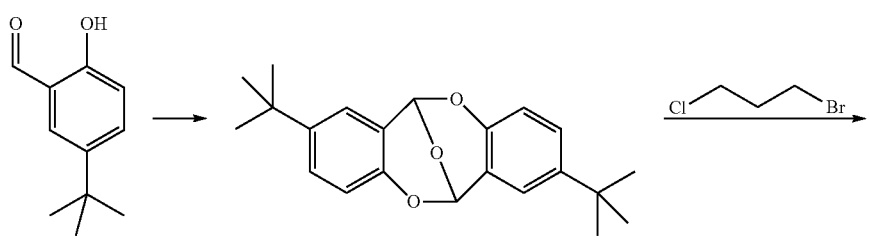
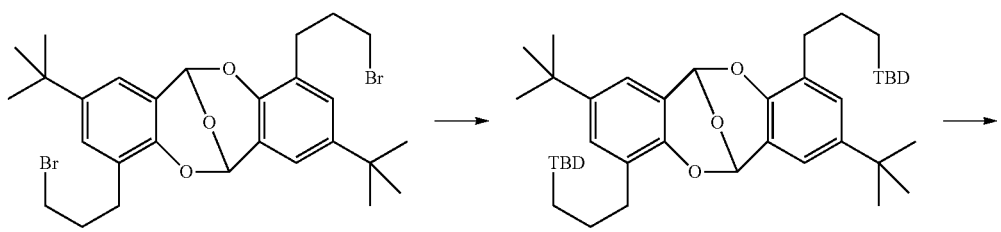 →
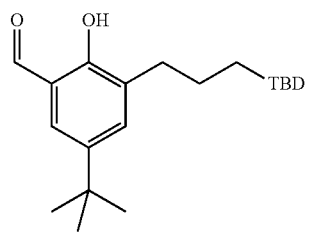
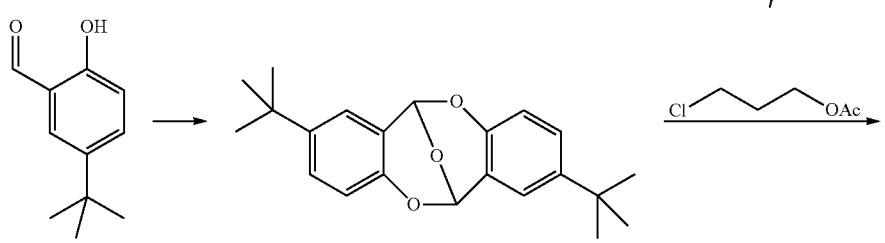
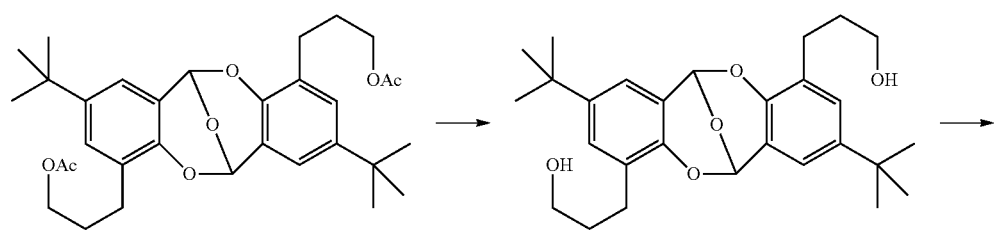 →

33
34
-continued
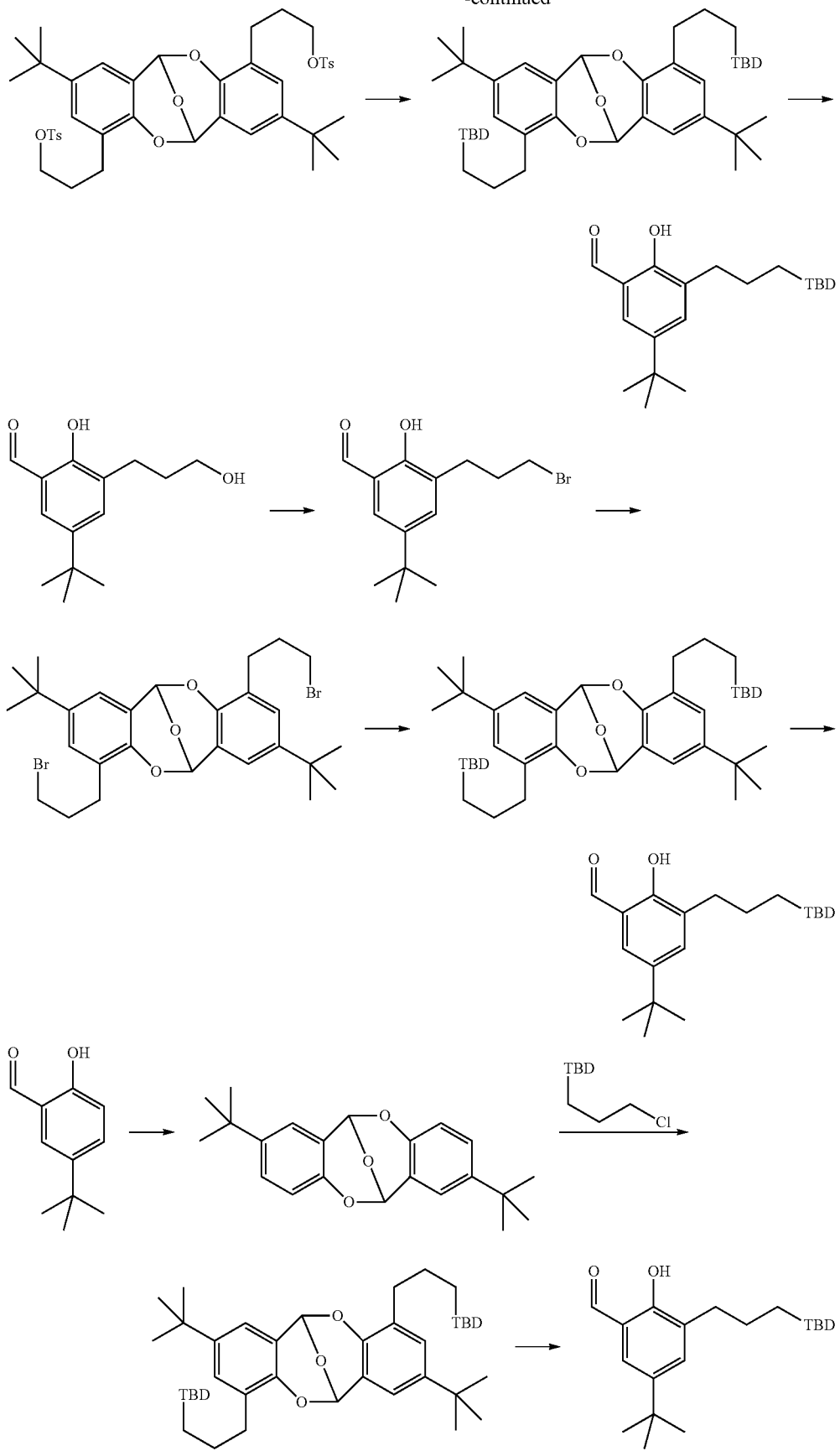

-continued
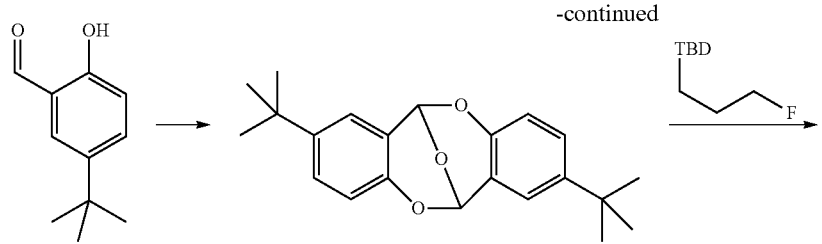
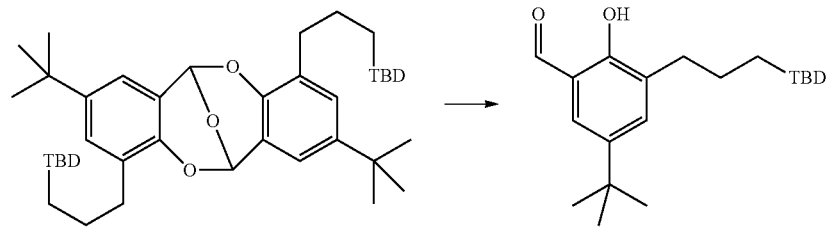
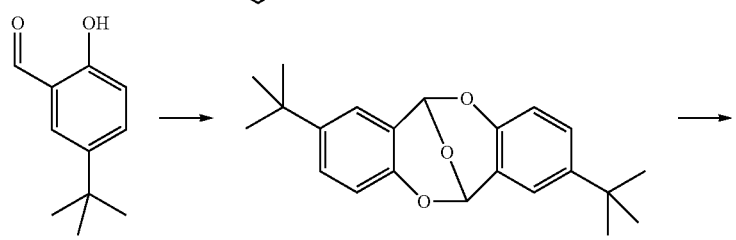
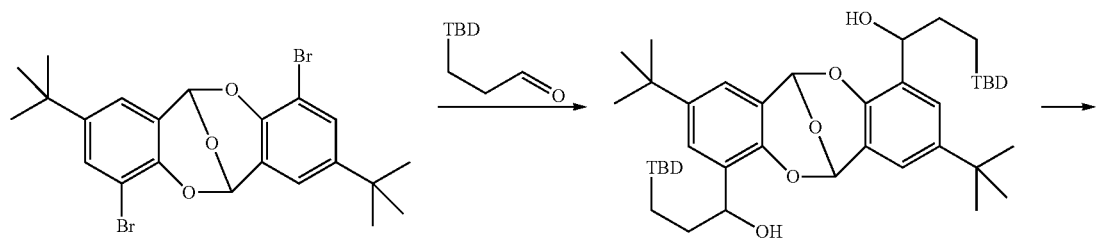
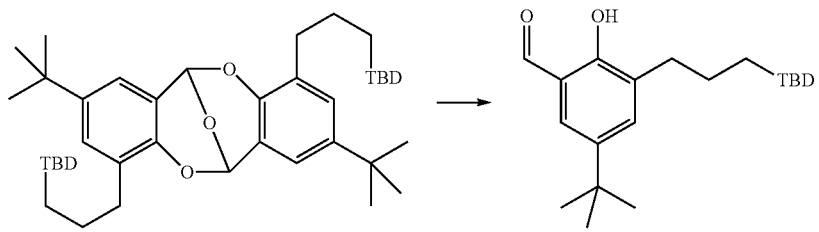
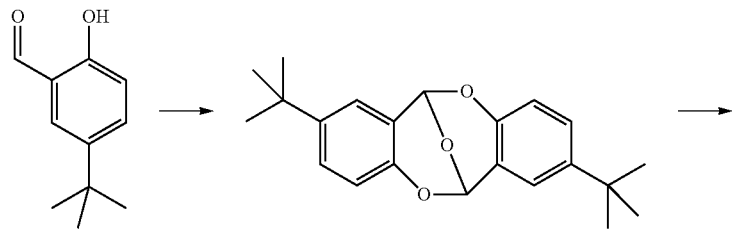
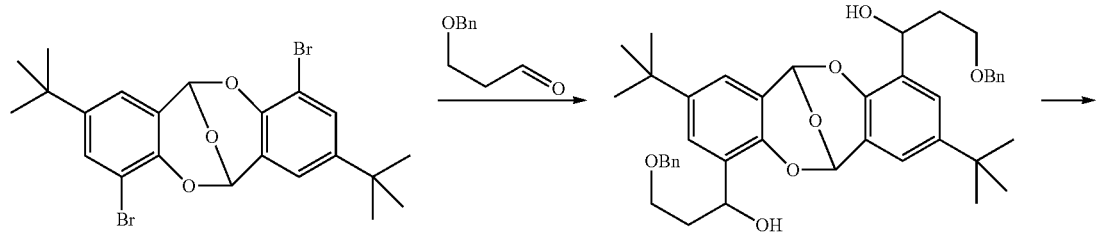

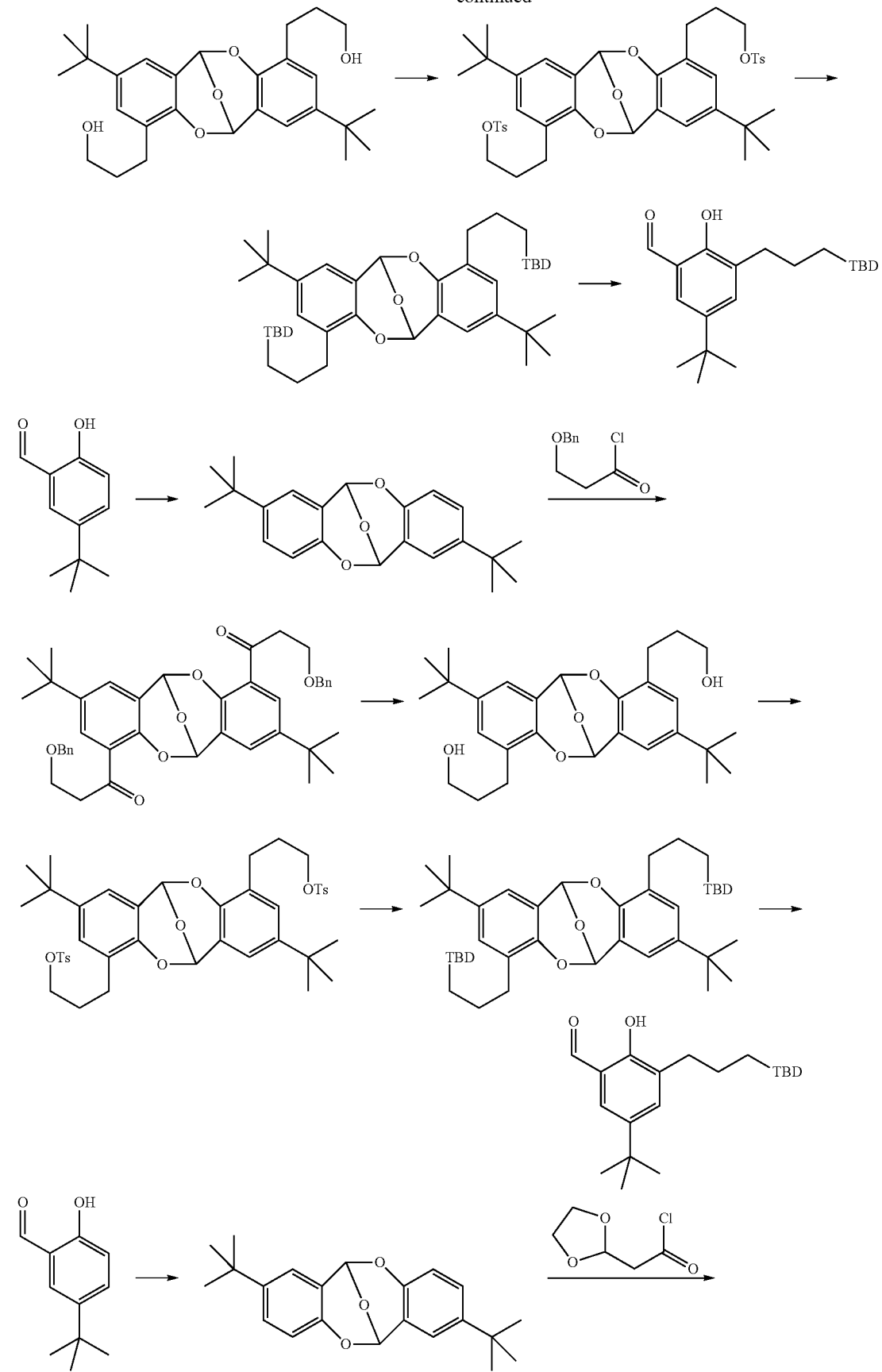

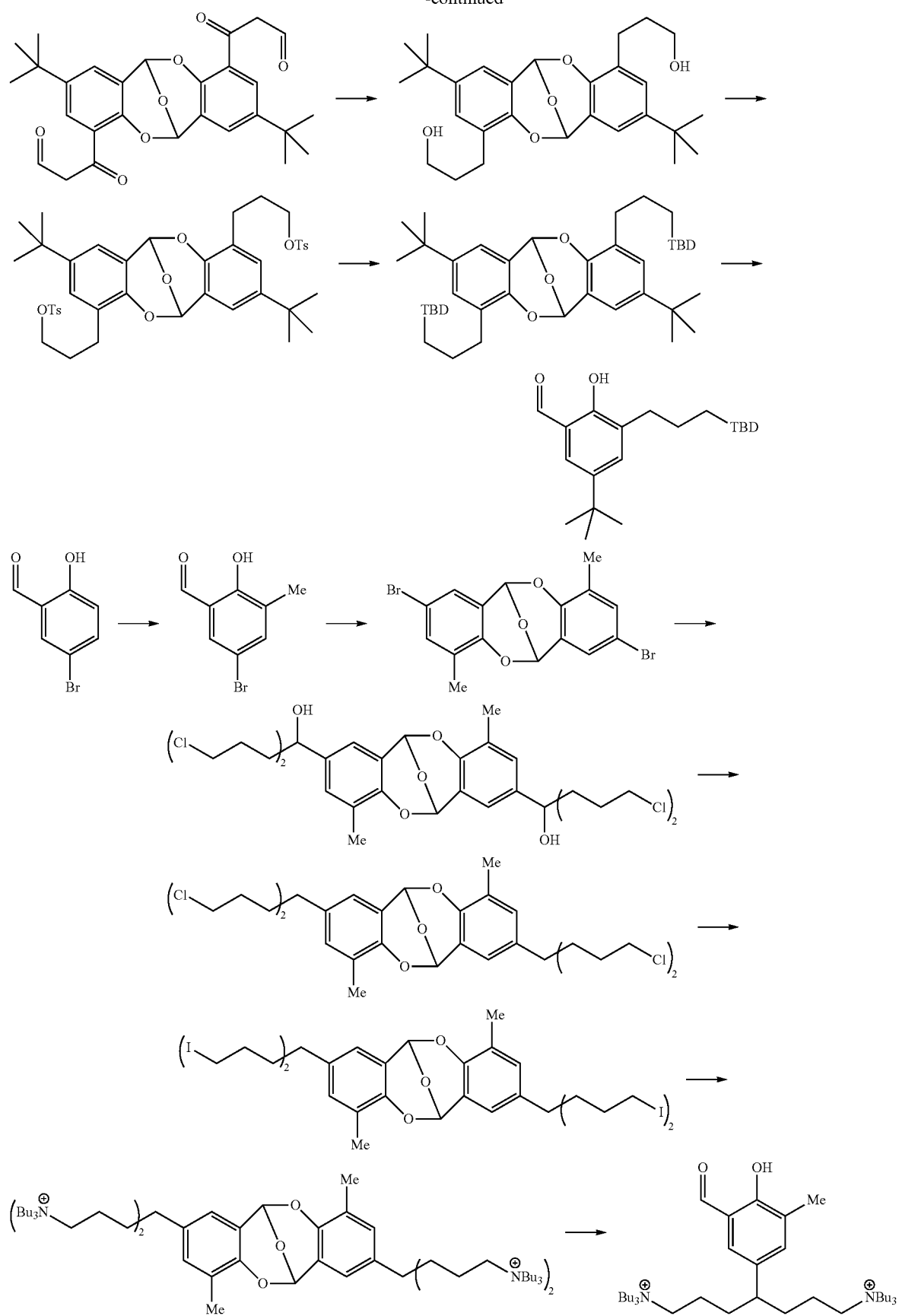

41     42
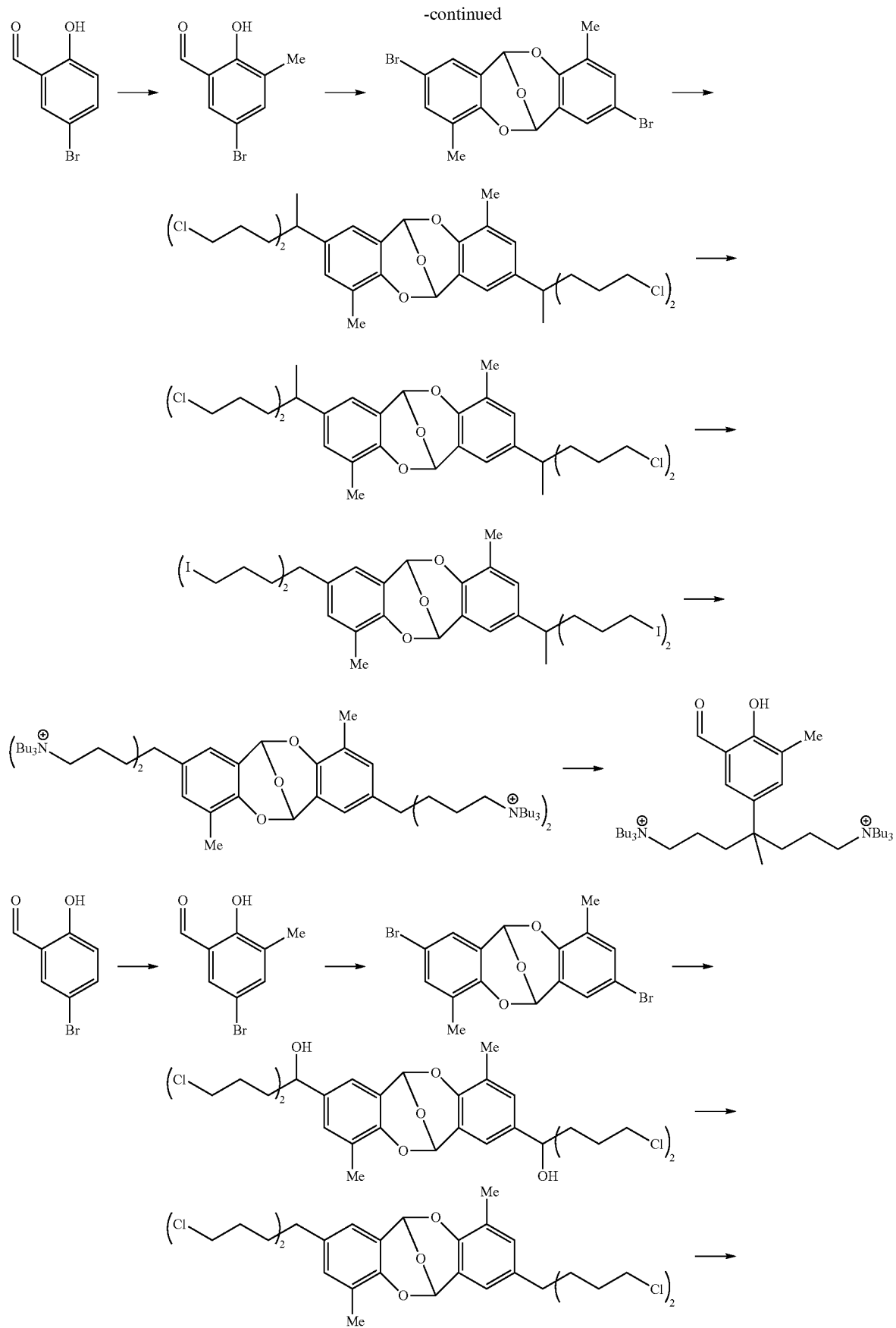

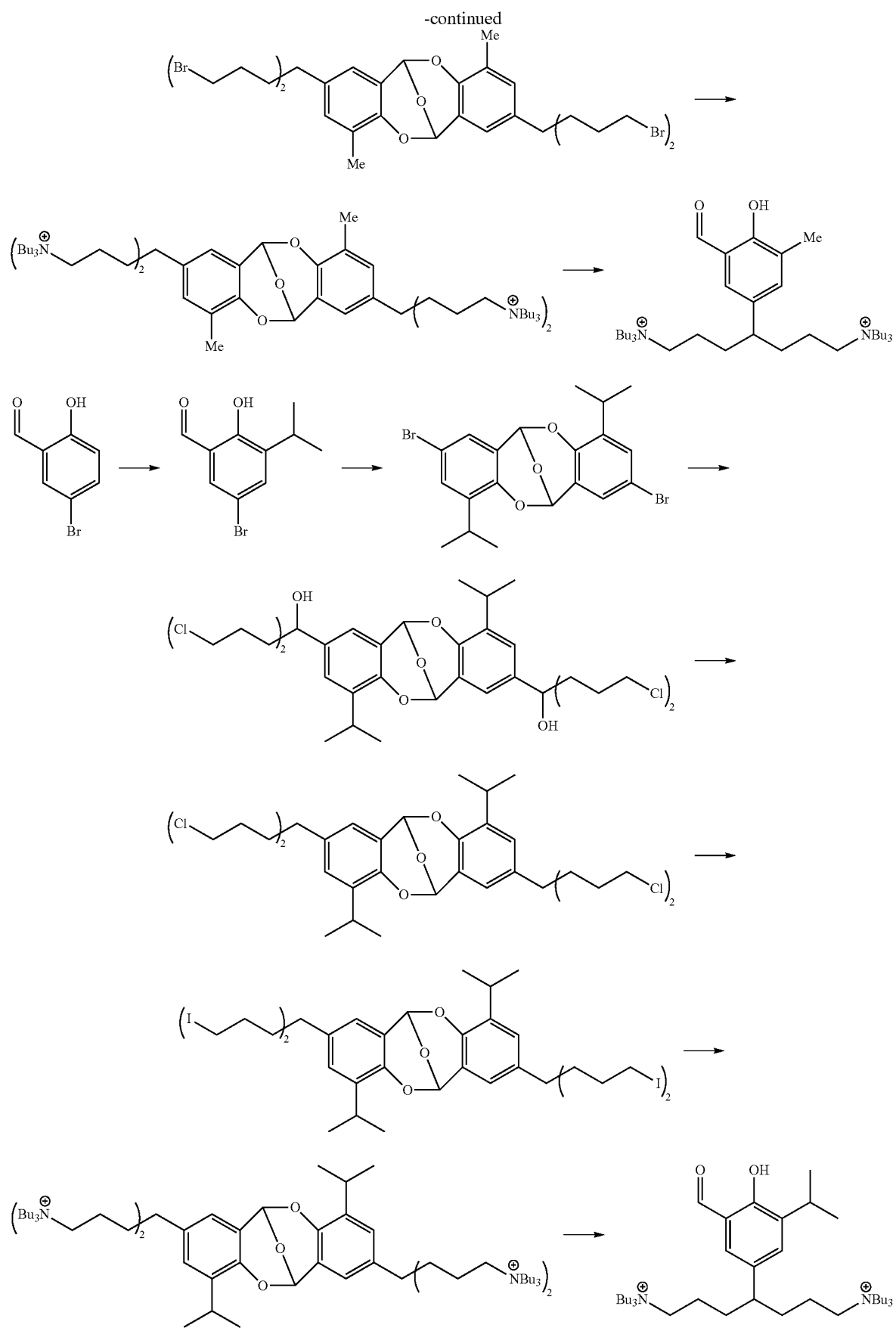

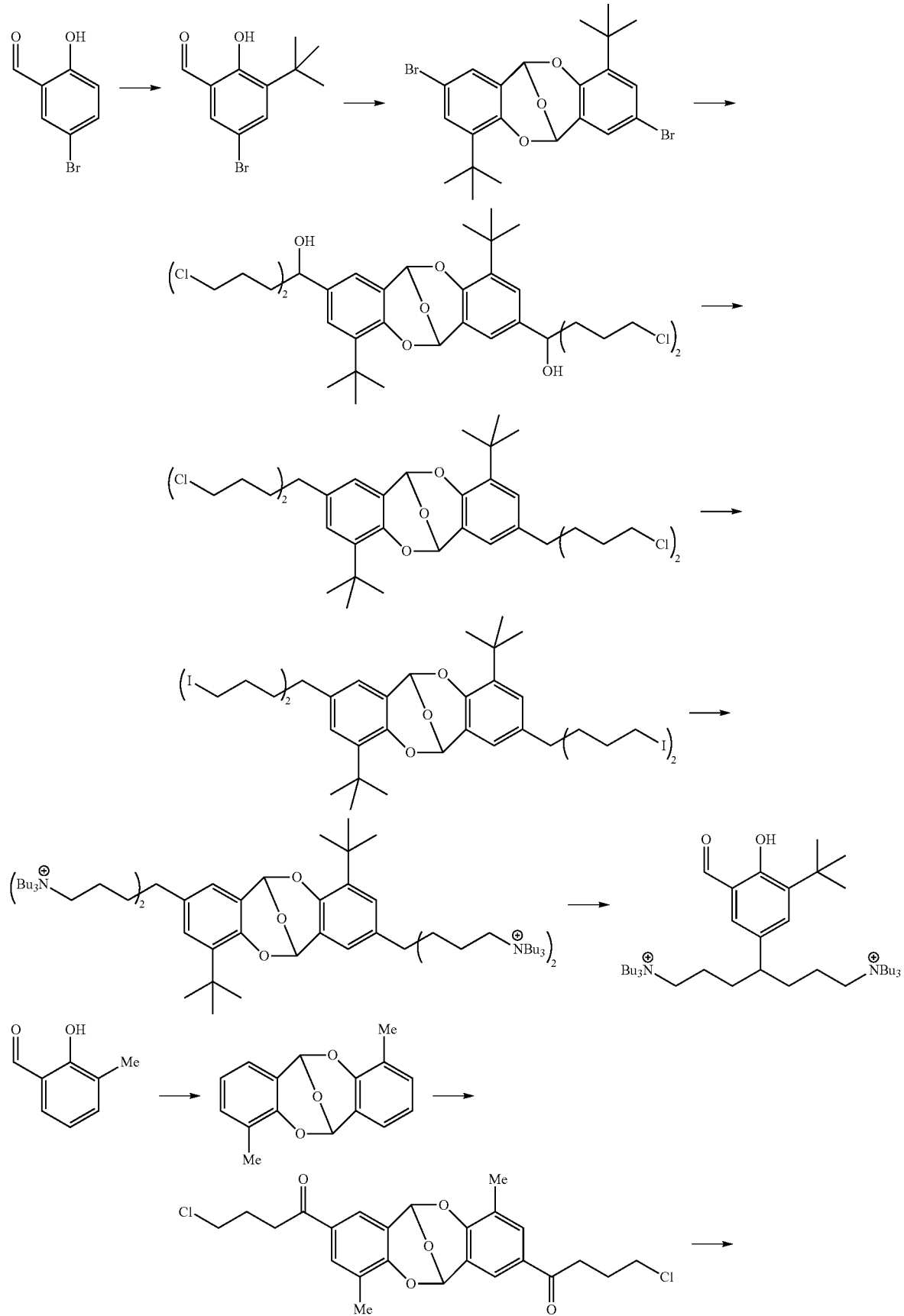

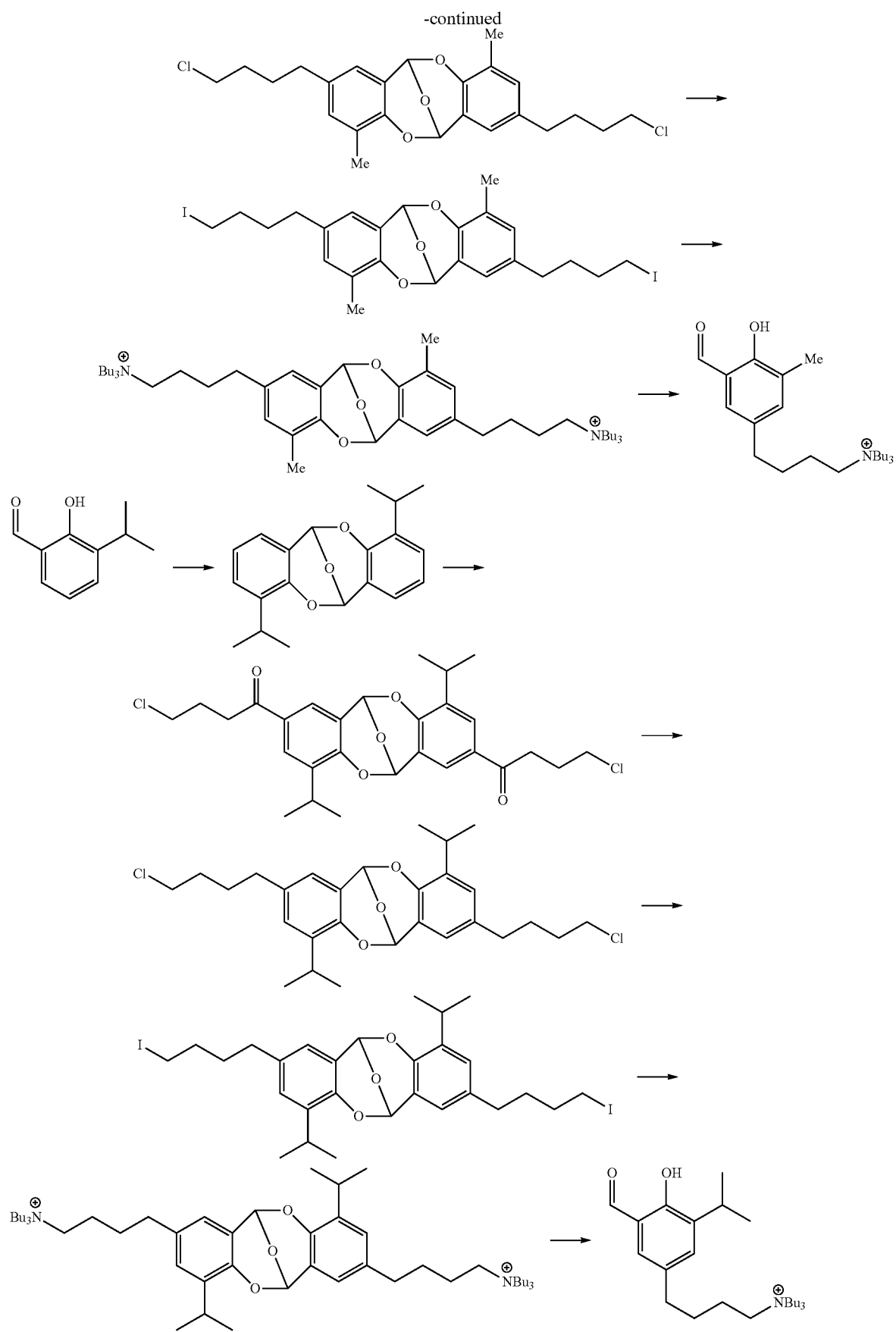

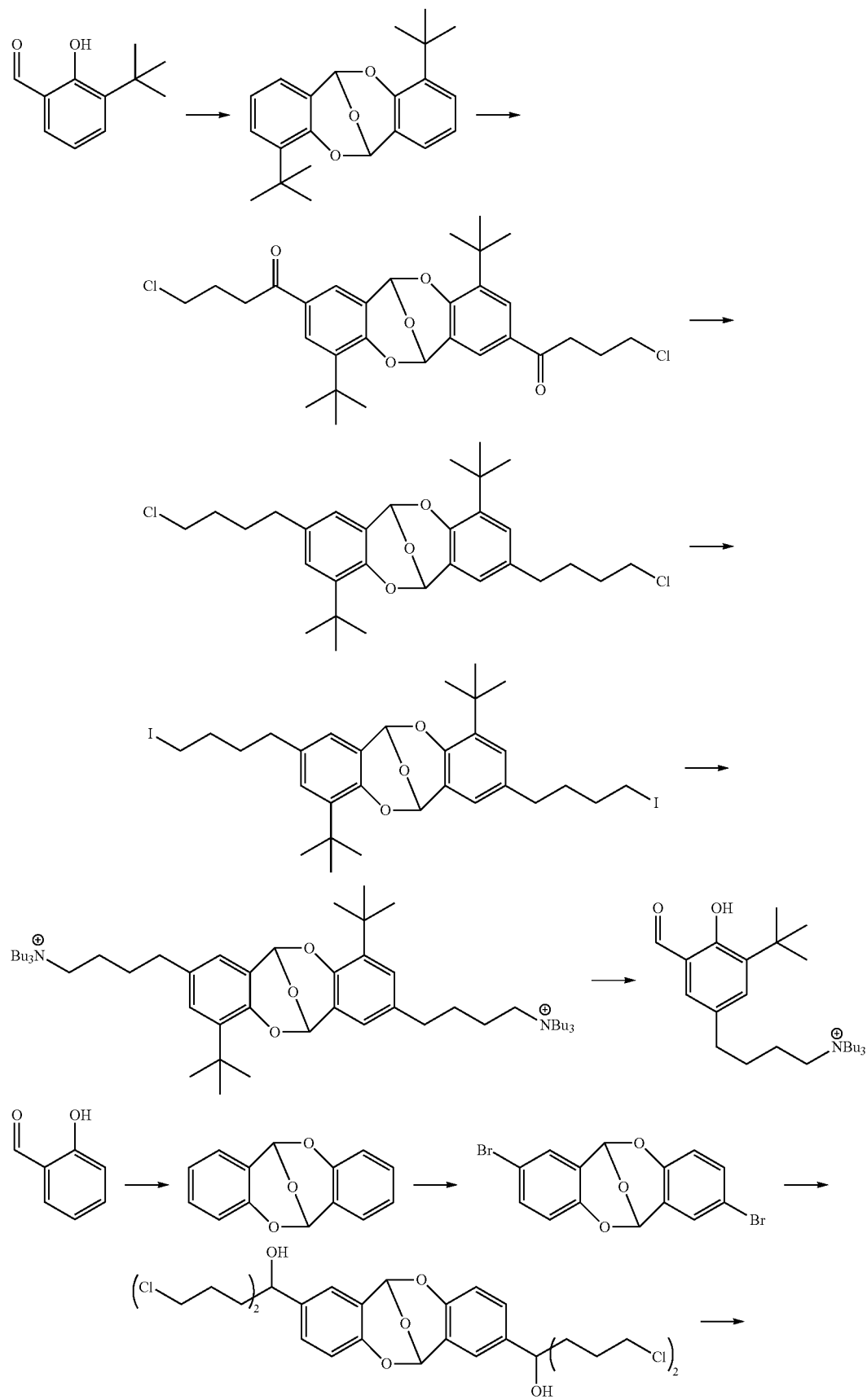

51 52
-continued
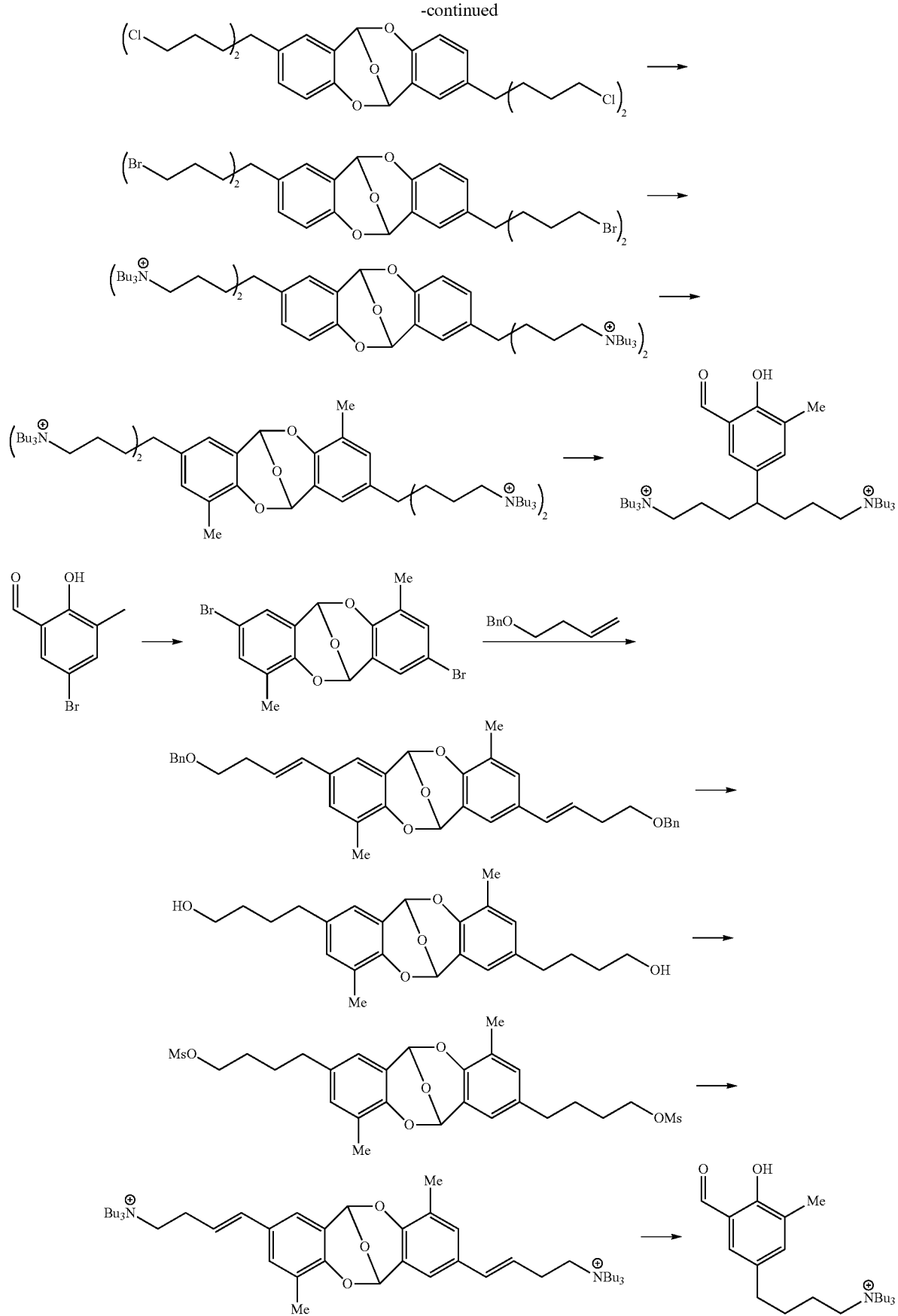

IV. Compositions of Matter

In certain embodiments, the present invention encompasses novel compositions of matter with utility in the production of substituted salicylaldehyde compounds. In certain embodiments, the present invention provides the anhydro dimers disclosed in the schemes and descriptions hereinabove.

In certain embodiments, the present invention encompasses anhydro dimers with utility in the production of salen catalysts. In certain embodiments, such compounds have a structure D1:

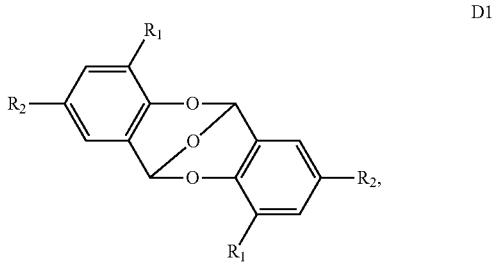

D1 wherein, $R_1$ and $R_2$ are independently selected from the group consisting of hydrogen, halogen, —$NO_2$, —CN, —Si($R^y$)$_3$, —$SR^y$, —S(O)$R^y$, —S(O)$_2R^y$, —$NR^yC(O)R^y$, —OC(O)$R^y$, —$CO_2R^y$, —NCO, —$N_3$, —$OR^y$, —OC(O)N($R^y$)$_2$, —N($R^y$)$_2$, —$NR^yC(O)R^y$, —$NR^yC(O)OR^y$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated or partially unsaturated polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur, 8- to 14-membered aryl; or an 8- to 10-membered bicyclic heteroaryl ring having 1-5 heteroatoms independently selected from nitrogen, oxygen, or sulfur, where each occurrence of $R^y$ is independently —H, or an optionally substituted radical selected from the group consisting of $C_{1-6}$ aliphatic, 3- to 7-membered heterocyclic, phenyl, and 8- to 10-membered aryl, and where two or more adjacent $R^y$ groups can be taken together to form an optionally substituted saturated, partially unsaturated, or aromatic 5- to 12-membered ring containing 0 to 4 heteroatoms, with the proviso that $R^1$ and $R^2$ are not both hydrogen.

In certain embodiments, in compounds of formula D1, at least one of $R_1$ and $R_2$ is an optionally substituted radical selected from the group consisting of $C_{1-20}$ aliphatic and $C_{1-20}$ heteroaliphatic. In certain embodiments, for compounds of formula D1, $R_1$ and $R_2$ are independently optionally substituted radicals selected from the group consisting of $C_{1-20}$ aliphatic and $C_{1-20}$ heteroaliphatic.

In certain embodiments, for compounds of formula D1, at least one of $R_1$ and $R_2$ is t-butyl. In certain embodiments, for compounds of formula D1, $R_1$ and $R_2$ are both t-butyl.

In certain embodiments, the present invention provides anhydro dimers with utility in the production of salen catalysts. In certain embodiments, such compounds have any of structures D2 through D8:

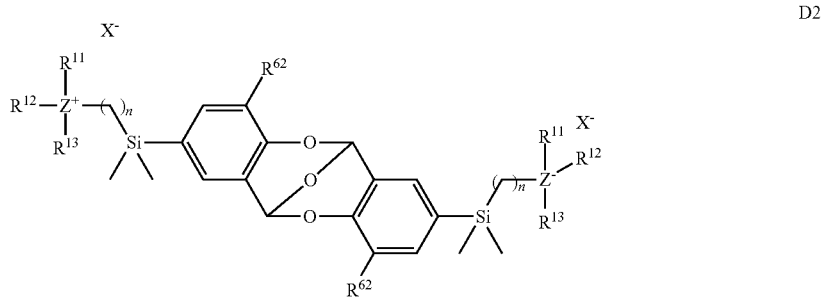

D2

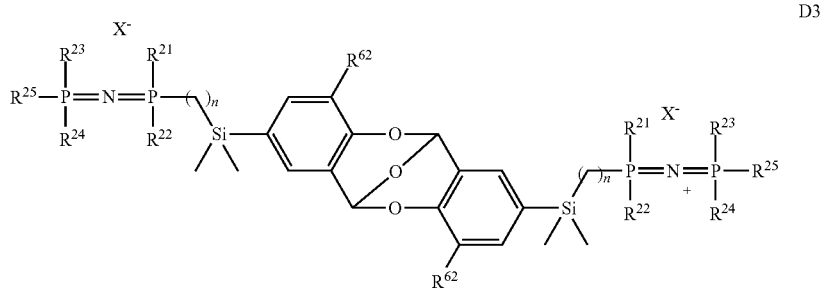

D3

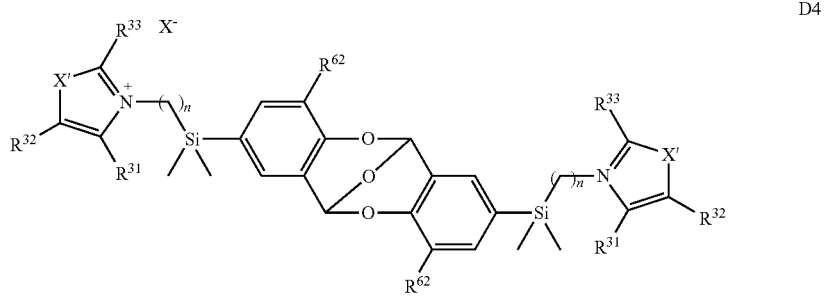

D4

-continued

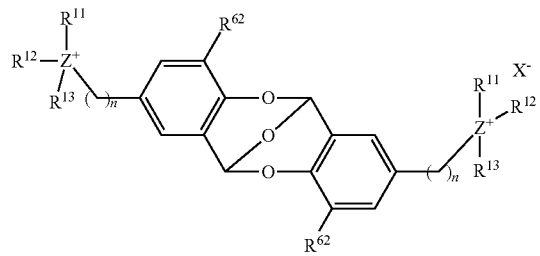
D5

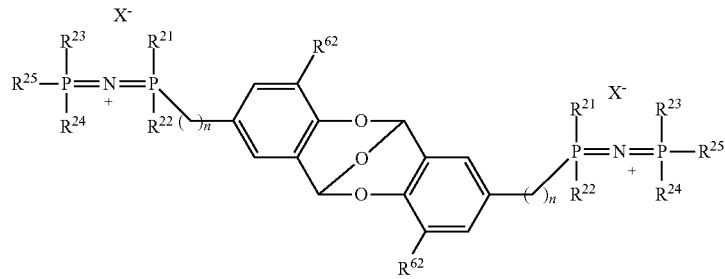
D6

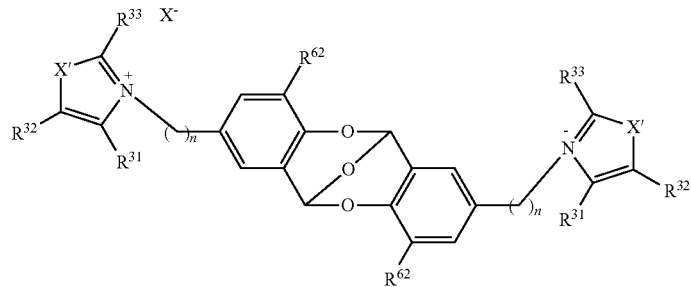
D7

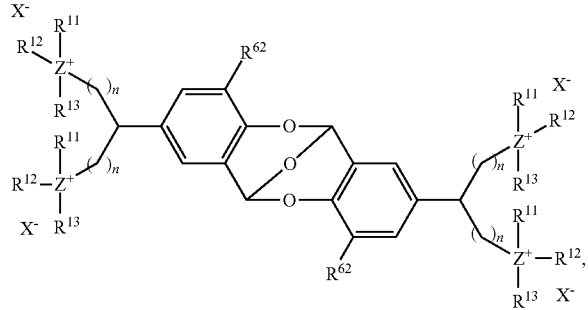
D8 wherein

Z is nitrogen or phosphorus, wherein the formal charge on Z satisfies valency requirements;

X is halogen; $C_6$-$C_{20}$ aryloxy; $C_6$-$C_{20}$ aryloxy having one or more functional moieties selected from the group consisting of halogen, nitrogen, oxygen, silicon, sulfur and phosphorus; $C_1$-$C_{20}$ carboxy; $C_1$-$C_{20}$ carboxy having one or more functional moieties selected from the group consisting of halogen, nitrogen, oxygen, silicon, sulfur and phosphorus; $C_1$-$C_{20}$ alkoxy; $C_1$-$C_{20}$ alkoxy having one or more functional moieties selected from the group consisting of halogen, nitrogen, oxygen, silicon, sulfur and phosphorus; $C_1$-$C_{20}$ alkylsulfonato; $C_1$-$C_{20}$ alkylsulfonato having one or more functional moieties selected from the group consisting of halogen, nitrogen, oxygen, silicon, sulfur and phosphorus; $C_1$-$C_{20}$ amido; or $C_1$-$C_{20}$ amido having one or more functional moieties selected from the group consisting of halogen, nitrogen, oxygen, silicon, sulfur and phosphorus;

$R^{11}$, $R^{12}$, $R^{13}$, $R^{21}$, $R^{22}$, $R^{23}$, $R^{24}$ and $R^{25}$ are each independently hydrogen; oxo; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus; or a metalloid radical of group XIV metal substituted by hydrocarbyl, two of $R^{11}$, $R^{12}$ and $R^{13}$, or two of $R^{21}$, $R^{22}$, $R^{23}$, $R^{24}$ and $R^{25}$ being optionally fused together to form a bridged structure;

$R^{31}$, $R^{32}$ and $R^{33}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; C7-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus; or a metalloid radical of group XIV metal substituted by hydrocarbyl, two of $R^{31}$, $R^{32}$ and $R^{33}$ being optionally fused together to form abridged structure;

$R^{62}$ is hydrogen, methyl, ethyl, n-propyl, isopropyl or tert-butyl;

n is from 1 to 20;

X' is oxygen, sulfur or N—R; and

R is hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus.

In certain embodiments, the invention encompasses anhydro dimers with any of structures D9 through D13:

D9

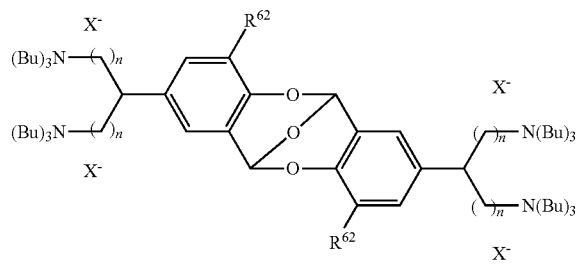

D10

D11

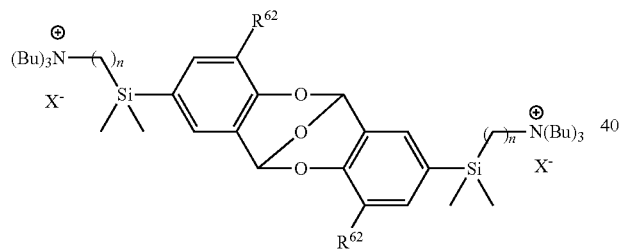

D12

D13 wherein

X, n, and $R^{62}$ are as defined above.

In certain embodiments, the invention encompasses anhydro dimers with any of structures D14 through D18:

D14

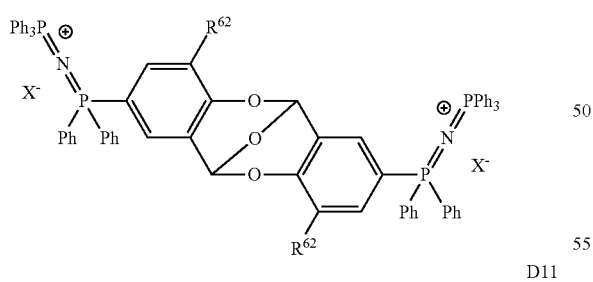

D15

D16

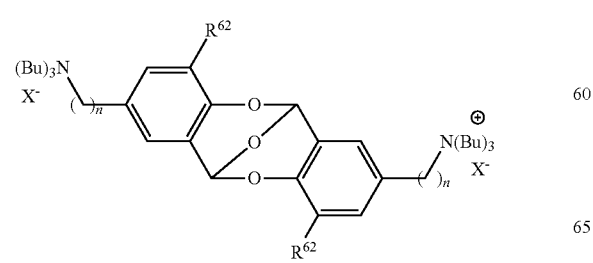

-continued

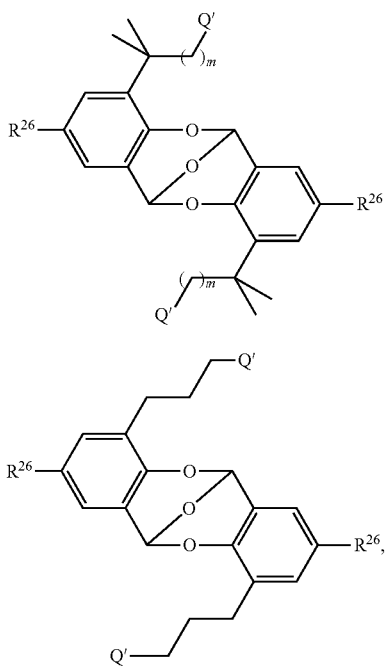

wherein, $R^{26}$ is selected from the group consisting of: hydrogen, halogen, optionally substituted $C_{1-20}$ aliphatic, and optionally substituted aryl;

$R^a$ and $R^b$ are, independently at each occurrence, selected from the group consisting of hydrogen, halogen, and optionally substituted $C_{1-4}$ aliphatic;

Q' is selected from the group consisting of: halogen, hydroxyl, sulfonate ester, a neutral or cationic nitrogen-containing functional group, and a neutral or cationic phosphorous-containing functional group; and m is from 1 to 10.

In certain embodiments, for compounds of formulae D14-D18, Q is selected from the group consisting of: bromine, chlorine, iodine, —OH, —$OSO_2R$, —$N(R)_2$, —$N(R)_3^+$, —$P(R)_3^+$, substituted guanidine, guanidinium, and amidine. In certain embodiments, in compounds of formulae D14-D18, Q' is hydroxyl. In certain embodiments, in compounds of formulae D14-D18, Q' is bromine. In certain embodiments, for compounds of formulae D14-D18, Q' is a guanidine. In certain embodiments, for compounds of formulae D14-D18, Q' is TBD. In certain embodiments, for compounds of formulae D14-D18, Q' is [N-methyl TBD]$^+$. In certain embodiments, for compounds of formulae D14-D18, Q' is trialkylammonium.

In certain embodiments, for compounds of formulae D14-D18, $R^{26}$ is selected from the group consisting of: —H, halogen, methyl, ethyl, n-propyl, i-propyl, n-butyl, sec-butyl, and t-butyl. In certain embodiments, for compounds of formulae D14-D18, $R^{26}$ is t-butyl.

In certain embodiments, for compounds of formulae D14-D18, n is an integer between 1 and 6. In certain embodiments, for compounds of formulae D14-D18, n is an integer between 2 and 5. In certain embodiments, for compounds of formulae D14-D18, n is 3 or 4.

EXAMPLES

Example 1

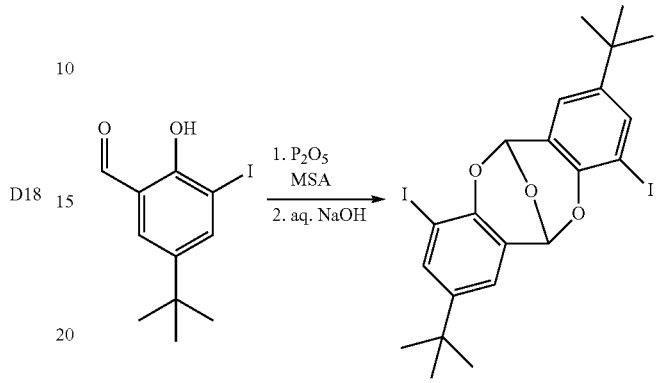

A mixture of 5-tert-butyl-2-hydroxy-3-iodobenzaldehyde (8.5 g, 28.1 mmol) and Eaton's reagent (7.5% w/w, 30 mL) was stirred at ambient temperature for 2.5 h. The reaction mixture was added dropwise to a cold (0-5° C.) solution of NaOH (24 g, 600 mmol) in water (45 mL). After the addition was complete, the solid that formed was collected by vacuum filtration and the filter cake was washed well with water (3×30 mL). The anhydro dimer was obtained as a tan powder after drying (5.4 g, 65%). $^1$H NMR (400 MHz, $CDCl_3$): δ 1.27 (s, 18 H), 6.37 (s, 2H), 7.32 (d, 2H, J=2.2 Hz), 7.71 (d, 2H, J=2.2 Hz).

Example 2

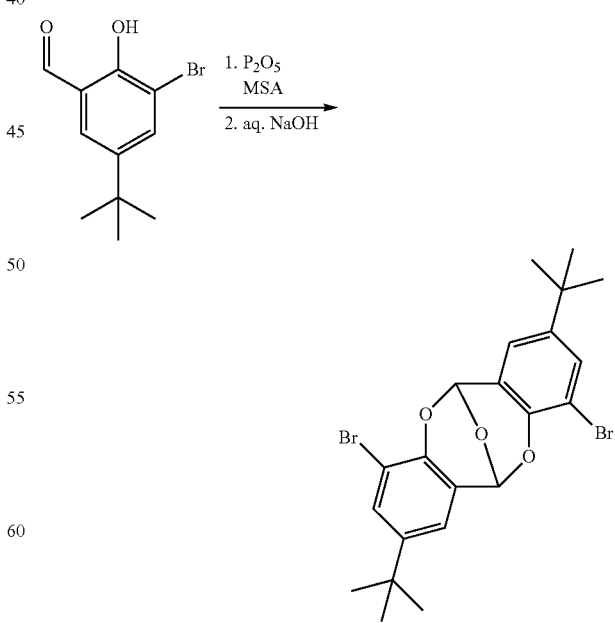

A mixture of 5-tert-butyl-3-bromo-2-hydroxybenzaldehyde (5 g, 19.4 mmol) and Eaton's reagent (7.5% w/w, 20 mL) was stirred at ambient temperature for 5 h. The reaction mixture was added dropwise to a cold (0-5° C.) solution of NaOH (16 g, 400 mmol) in water (35 mL). After the addition was complete, the solid that formed was collected by vacuum filtration and the filter cake was washed well with water (3×30 mL). The anhydro dimer was obtained as a tan powder in quantitative yield after drying (4.83 g, 100%). $^1$H NMR (400 MHz, CDCl$_3$): δ 1.27 (s, 18 H), 6.42 (s, 2H), 7.30 (d, 2H, J=2.2 Hz), 7.51 (d, 2H, J=2.2 Hz).

Example 3

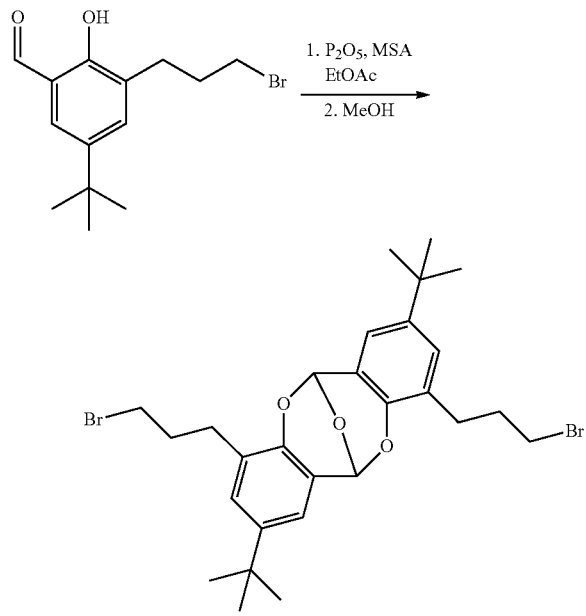

To a solution of 5-tert-butyl-3-(3-bromopropyl)-2-hydroxybenzaldehyde (5 g, 16.8 mmol) in EtOAc (9 mL) was added Eaton's reagent (5.5 mL). The reaction mixture was heated at 65 C for 4.5 h and then cooled to 0-5° C. Cold MeOH (10 mL) was added and the resulting slurry was filtered. The filter cake was washed with cold MeOH (2×10 mL) and the filter cake was dried to give the anhydro dimer as a white powder (3.25 g, 67%). $^1$H NMR (300 MHz, CDCl$_3$): δ 1.27 (s, 18 H), 2.07 (m, 2H), 2.71 (m, 2H), 3.29 (m, 2H), 6.32 (s, 2H), 7.13 (d, 2H, J=2.4 Hz), 7.15 (d, 2H, J=2.4 Hz).

Example 4

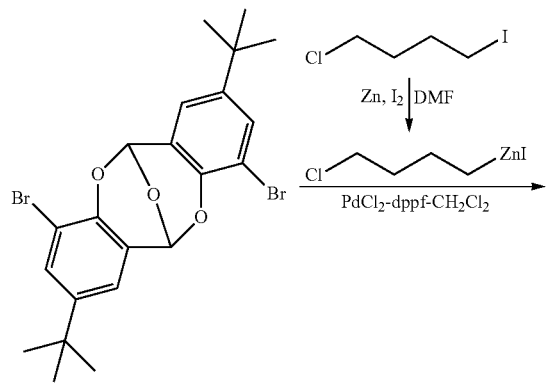

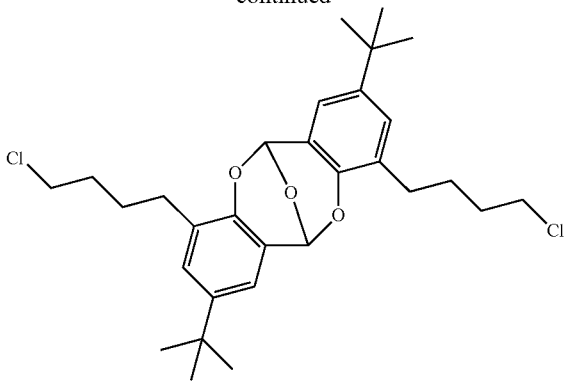

Zinc powder (1.28 g, 19.6 mmol) suspended in DMF (7 mL) was treated with I$_2$ (0.21 g, 1 mmol) under nitrogen at ambient temperature. When the red color dissipated, the mixture was warmed to 50° C., and a charge of 1-chloro-4-iodobutane (2 mL, 16.3 mmol) was added. After two hours, the anhydro dimer of 5-tert-butyl-3-bromo-2-hydroxybenzaldehyde (2.3 g, 4.6 mmol) and PdCl$_2$-dppf-CH$_2$Cl$_2$ (0.37 g, 0.45 mmol) were added. Heating at 60° C. was continued for 17 h. Afterwards, water was added (20 mL) and a precipitate formed. The material was collected by vacuum filtration and dried to give the desired product in high yield (2.18 g, 90%). $^1$H NMR (400 MHz, CDCl$_3$): δ 1.26 (s, 18 H), 1.65 (m, 2H), 1.76 (m, 2H), 2.58 (m, 2H), 3.49 (t, 2H, J=6.5 Hz), 6.32 (s, 2H), 7.08 (d, 2H, J=2.4 Hz), 7.12 (d, 2H, J=2.4 Hz).

Example 5

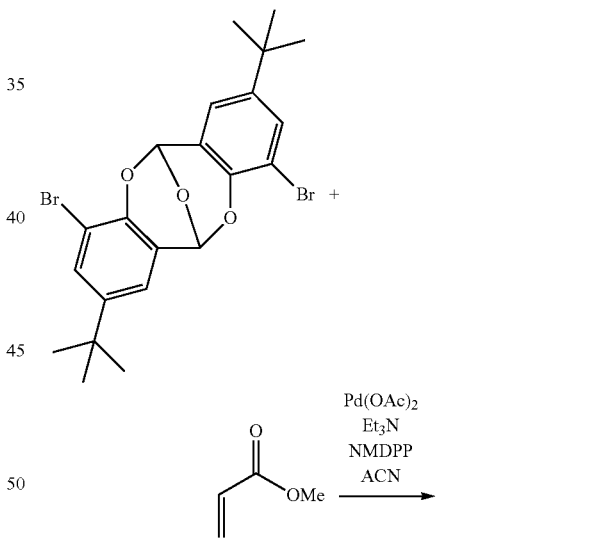

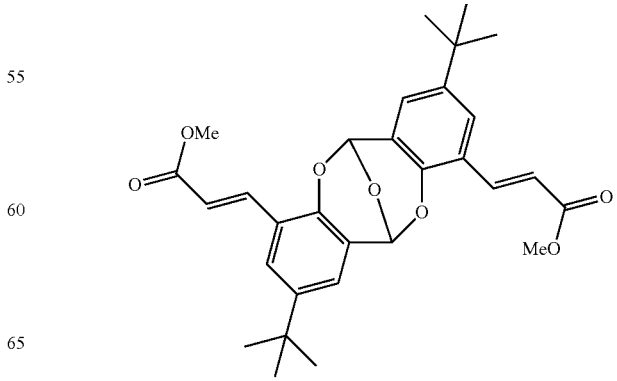

A flask was charged with Pd(OAc)$_2$ (2.2 mg, 0.01 mmol), neomenthyldiphenylphosphine (13 mg, 0.04 mmol)), methyl acrylate (55 mg, 0.64 mmol), Et$_3$N (55 mg, 0.54 mmol), and the anhydro dimer of 5-tert-butyl-3-bromo-2-hydroxybenzaldehyde (55 mg, 0.11 mmol). The contents were suspended in ACN (1.25 mL) under N$_2$ and heated at 95° C. for 14 h. The mixture was cooled to ambient temperature and the resulting slurry was filtered. The filter cake was washed with heptane (0.5 mL) and dried to provide the desired product as a white solid (42 mg, 0.083 mmol, 75%). $^1$H NMR (400 MHz, CDCl$_3$): δ 1.26 (s, 18 H), 3.82 (s, 6H), 6.41 (s, 2H), 6.57 (d, 2H, J=16 Hz), 7.35 (d, 2H, J=2.4 Hz), 7.50 (d, 2H, J=2.4 Hz), 7.88 (d, 2H, J=16 Hz).

Example 6

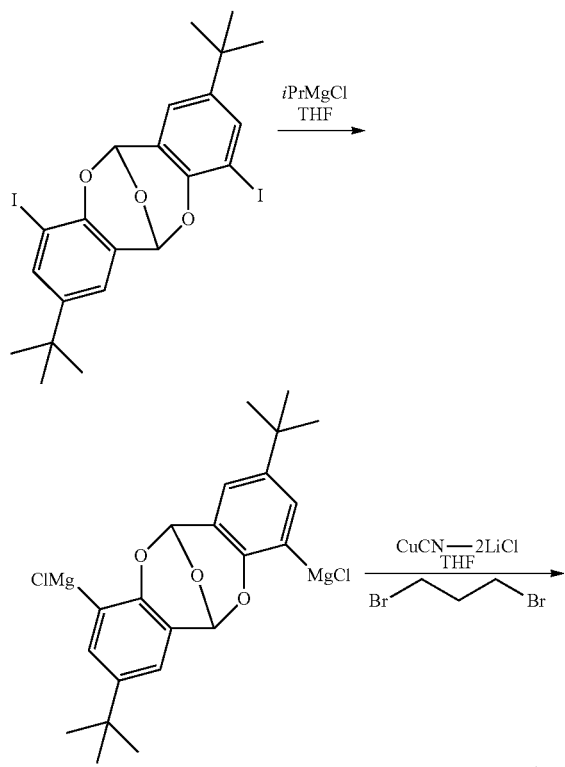

The anhydro dimer of 5-tert-butyl-2-hydroxy-3-iodobenzaldehyde (150 mg, 0.25 mmol) was dissolved in THF (0.25 mL) and treated with a solution of iPrMgCl in THF (2 M, 0.66 mmol) at ambient temperature under nitrogen. Within 0.5 h, a solution of CuCN-2LiCl in THF (1 M, 0.5 mmol) was added and the mixture was allowed to stir another 0.5 h. A charge of 1,3-dibromopropane (0.067 mL, 0.66 mmol) was added and the mixture was heated to 60° C. After 2 h, an HPLC aliquot showed formation of the desired product as determined by comparison with the HPLC chromatogram of an authentic sample.

Example 7

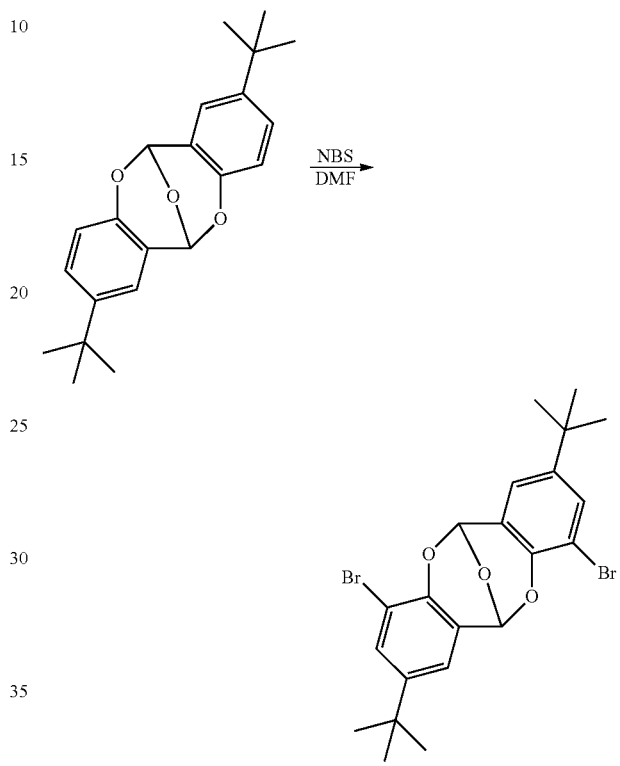

The anhydro dimer of 5-tert-butyl-2-hydroxybenzaldehyde (630 mg, 1.9 mmol) and N-bromosuccinamide (665 mg, 3.7 mmol) was dissolved in DMF (4 mL) at room temperature. After 3 h, the temperature was gradually increased to 60° C. More NBS (1.75 g, 9.7 mmol) was added to the reaction over 7 h. The reaction was diluted with water and the precipitate that formed was collected by vacuum filtration and washed well with water. After drying, the desired product was obtained as a powder (710 mg, 76%). $^1$H NMR (400 MHz, CDCl$_3$): δ 1.27 (s, 18H), 6.42 (s, 2H), 7.3 (d, J=2.1 Hz, 2H), 7.51 (d, J=2.1 Hz, 2H).

Example 8

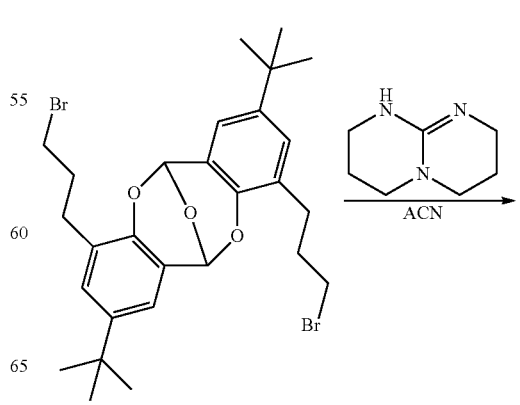

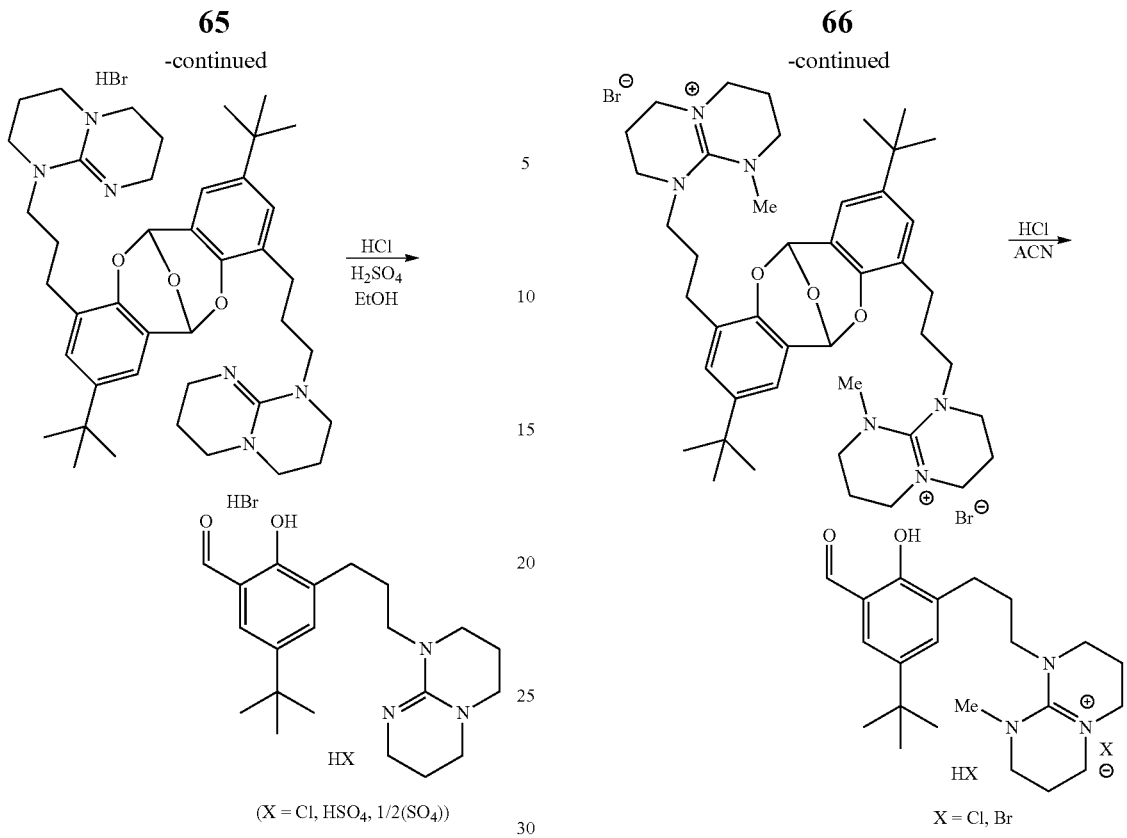

(X = Cl, HSO₄, 1/2(SO₄))

The anhydro dimer of 5-tert-butyl-3-(3-bromopropyl)-2-hydroxybenzaldehyde (1 g, 1.7 mmol) was combined with 1,5,7-triazabicyclo[4.4.0]dec-5-ene (TBD) (0.53 g, 3.8 mmol) in 10 mL acetonitrile. The mixture was heated to 65° C. and held for 16 h. The solution was then washed with hexanes (1×10 mL) and concentrated to an oil. The oil was taken up in EtOH and treated with 1 M HCl (20 mL) at 65° C. After 1 h, conc. HCl (2 mL) was added. After 3 h, conc. H₂SO₄ (1 mL) was added and the reaction was stirred at 65° C. for another 3 h. The solvent was then removed and EtOAc was added to give a biphasic mixture. The aqueous layer was adjusted to pH 7 with aq. NaOH. The layers were separated and the aqueous was extracted again with dichloromethane. The organic extracts were concentrated to yield an oil (1.22 g). ¹H NMR (400 MHz, CDCl₃): δ 1.23 (s, 9H), 1.89 (m, 4H), 1.99 (m, 2H), 2.69 (dd, J=7.5, 8.9 Hz, 2H), 3.27 (m, 6H), 3.41 (t, J=7.3 Hz, 2H), 3.57 (t, J=7.3 Hz, 2H), 7.32 (d, J=2.5 Hz, 1H), 7.48 (d, J=2.5 Hz, 1H), 9.90 (s, 1H).

Example 9

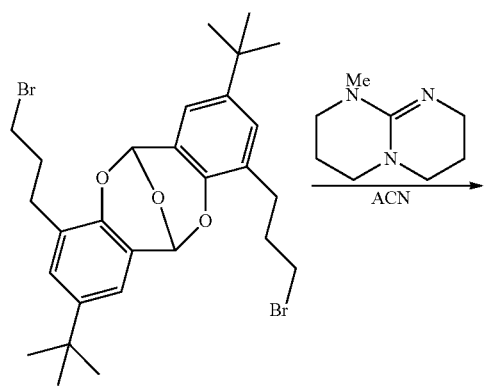

The anhydro dimer of 5-tert-butyl-3-(3-bromopropyl)-2-hydroxybenzaldehyde (0.5 g, 0.86 mmol) was combined with 7-methyl-1,5,7-triazabicyclo[4.4.0]dec-5-ene (MeTBD) (0.37 g, 2.6 mmol) in 1.5 mL acetonitrile. The mixture was heated to 70° C. and held for 5 h. The reaction was then allowed to cool to room temperature overnight. Concentrated HCl (0.8 mL, 9.9 mmol) was added and the mixture was heated over the range of 50-65° C. for 8 h with an additional charge of conc. HCl (0.4 mL, 4.9 mmol) after 5 h. The reaction yielded the desired product as a solution in aq. HCl and ACN. Low resolution mass spec (m/z): [M⁺]372.3, [(2M-H)⁺]743.0.

Other Embodiments

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:
1. A method comprising the steps of:
   a) providing a salicylaldehyde, and
   b) forming an anhydro dimer of the provided salicylaldehyde compound, and
   c) performing one or more chemical transformations on the anhydro dimer, and
   d) hydrolyzing the anhydro dimer to provide a salicylaldehyde different from that provided in step a).
2. The method of claim 1, comprising the steps of:
   a) dehydrating a salicylaldehyde to form an anhydro dimer;
   b) alkylating at least one aromatic ring of the anhydro dimer in one or more positions; and c) hydrolyzing the alkylated anhydro dimer to recover an alkylated salicyladehyde.

3. The method of claim 2, wherein the step of alkylating the aromatic ring comprises reacting the anhydro dimer under Friedel Crafts alkylating conditions.

4. The method of claim 3, wherein the Friedel Crafts alkylating conditions comprise reacting the anhydro dimer with at least one compound selected from the group consisting of: alkenes, alcohols, alkyl halides, and mixtures of two or more of these in the presence of a promoter selected from the group consisting of Lewis acids and proton acids.

5. The method of claim 2, wherein the alkylation occurs equally on both salicylaldhyde molecules comprising the anhydro dimer.

6. The method of claim 2, wherein the alkylation occurs at the aromatic ring position ortho to the hydroxyl group of the starting salicylaldehyde.

7. The method of claim 2, wherein the alkylation occurs at the aromatic ring position para to the hydroxyl group of the starting salicylaldehyde.

8. The method of claim 2, wherein bis alkylation occurs at aromatic ring positions ortho and para to the hydroxyl group of the starting salicylaldehyde.

9. The method of claim 2, wherein the method comprises a first alkylating step using a first alkylating reagent and a second alkylating step using a second alkylating reagent wherein the first and second alkylating reagents are different.

10. The method of claim 9, wherein the first alkyating step introduces a substituent at the aryl position para to the phenol hydroxy group of the starting salicylaldehyde and the second alkylating step introduces a different substituent at the aryl position ortho to the phenol hydroxy group of the starting salicylaldehyde.

11. The method of claim 2, wherein the starting salicylaldehyde is substituted at the aryl position ortho to the phenol and the alkylation step introduces a substituent at the aryl position para to the phenol hydroxyl group.

12. The method of claim 2, wherein the starting salicylaldehyde is substituted at the aryl position para to the phenol and the alkylation step introduces a substituent at the aryl position ortho to the phenol hydroxyl group.

13. The method of claim 2, wherein the anhydro dimer formed in step (a) of claim 2 has a formula:

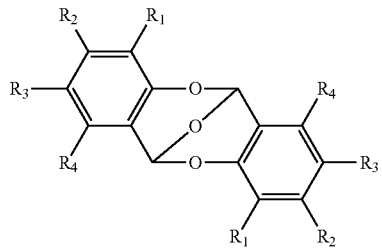

wherein at least one of $R_1$, $R_2$, $R_3$, and $R_4$ is —H, and the remainder are each independently selected from the group consisting of halogen, —$NO_2$, —CN, —Si($R^y$)$_3$, —$SR^y$, —S(O)$R^y$, —S(O)$_2R^y$, —$NR^yC(O)R^y$, —OC(O)$R^y$, —$CO_2R^y$, —NCO, —$N_3$, —OR$^y$, —OC(O)N($R^y$)$_2$, —N($R^y$)$_2$, —$NR^yC(O)R^y$, —$NR^yC(O)OR^y$; or an optionally substituted radical selected from the group consisting of C1-20 aliphatic; C1-20 heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where each occurrence of $R^y$ is independently —H, or an optionally substituted radical selected from the group consisting of $C_{1-6}$ aliphatic, 3- to 7-membered heterocyclic, phenyl, and 8- to 10-membered aryl, and where two or more adjacent $R^y$ groups can be taken together to form an optionally substituted saturated, partially unsaturated, or aromatic 5- to 12-membered ring containing 0 to 4 heteroatoms.

14. The method of claim 13, wherein $R^3$ is H in dehydrating step (a).

15. The method of claim 14, wherein $R^1$ in dehydrating step (a) is selected from the group consisting of optionally substituted $C_{1-20}$ aliphatic, and optionally substituted aryl.

16. The method of claim 15, wherein $R^1$ in dehydrating step (a) is selected from the group consisting of methyl, ethyl, n-propyl, isopropyl, n-butyl, sec-butyl, t-butyl, isoamyl, tert-amyl, and substituted phenyl.

17. The method of claim 13, wherein the alkylation at step (b) changes $R^3$ from —H to an optionally substituted aliphatic group.

18. The method of claim 17, wherein the optionally substituted aliphatic group introduced at $R^3$ is selected from the group consisting of optionally substituted $C_{1-20}$ aliphatic, and optionally substituted aryl.

19. A compound selected from:

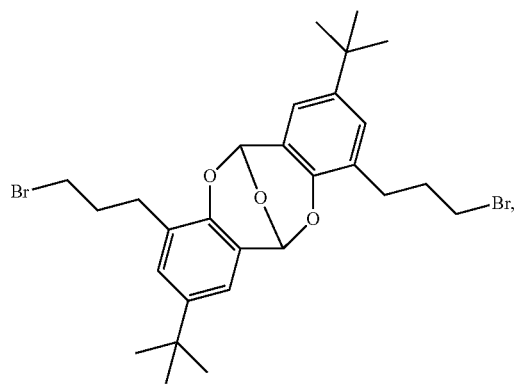

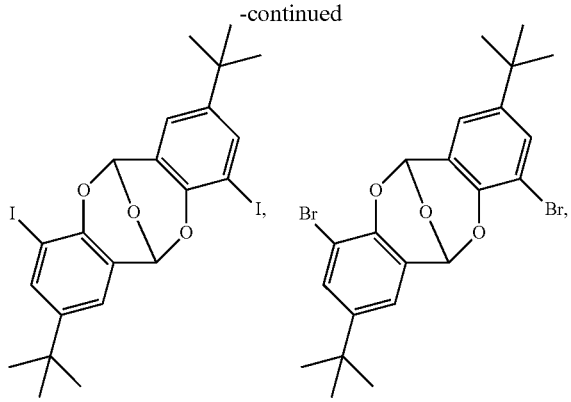
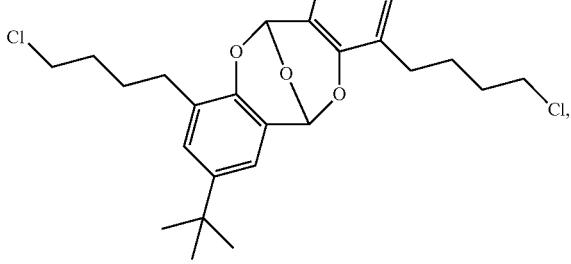
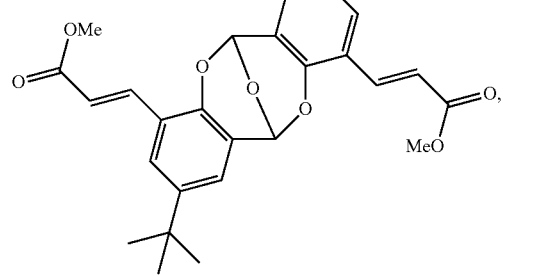
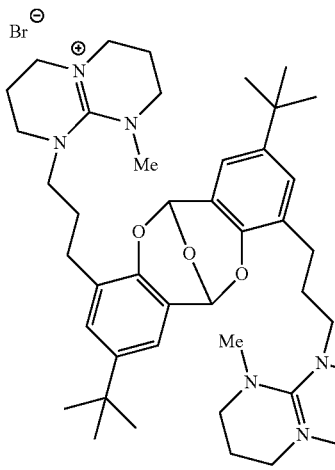
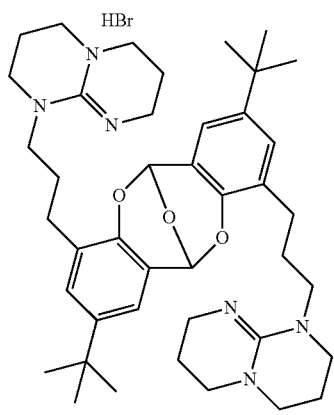
* * * * *